US008029787B2

(12) United States Patent
Salceda et al.

(10) Patent No.: US 8,029,787 B2
(45) Date of Patent: Oct. 4, 2011

(54) METHOD OF DIAGNOSING, MONITORING, STAGING, IMAGING AND TREATING VARIOUS CANCERS

(75) Inventors: Susana Salceda, San Jose, CA (US); Yongming Sun, San Jose, CA (US); Herve Recipon, San Francisco, CA (US); Robert Cafferkey, San Jose, CA (US)

(73) Assignee: diaDexus, Inc., South San Francisco, CA (US)

( * ) Notice: Subject to any disclaimer, the term of this patent is extended or adjusted under 35 U.S.C. 154(b) by 0 days.

(21) Appl. No.: 12/787,675

(22) Filed: May 26, 2010

(65) Prior Publication Data

US 2010/0284910 A1 Nov. 11, 2010

Related U.S. Application Data

(63) Continuation of application No. 09/763,978, filed as application No. PCT/US99/19655 on Sep. 1, 1999, now Pat. No. 7,737,255.

(60) Provisional application No. 60/098,880, filed on Sep. 2, 1998.

(51) Int. Cl.
*A61K 39/395* (2006.01)

(52) U.S. Cl. .................................................. 424/130.1

(58) Field of Classification Search ........................ None
See application file for complete search history.

(56) References Cited

U.S. PATENT DOCUMENTS

| 5,733,738 | A | 3/1998 | Niman | 435/7.23 |
|---|---|---|---|---|
| 5,733,748 | A | 3/1998 | Yu et al. | 435/70.1 |
| 5,939,258 | A | 8/1999 | Croce et al. | 435/6 |
| 6,468,546 | B1 | 10/2002 | Mitcham et al. | 424/277.1 |
| 6,488,931 | B1 | 12/2002 | Mitcham et al. | 424/184.1 |
| 6,528,253 | B1 | 3/2003 | Mitcham et al. | 435/6 |
| 6,670,463 | B1 | 12/2003 | Mitcham et al. | 536/23.5 |
| 6,699,664 | B1 | 3/2004 | Mitcham et al. | 435/6 |
| 6,962,980 | B2 | 11/2005 | Mitcham et al. | 530/387.1 |
| 2002/0034749 | A1 | 3/2002 | Billing-Mendel | 435/6 |
| 2002/0193299 | A1 | 12/2002 | Ashkenazi | 514/12 |
| 2002/0193300 | A1 | 12/2002 | Ashkenazi | 514/12 |
| 2003/0008297 | A1 | 1/2003 | Ashkenazi | 435/6 |
| 2003/0040473 | A1 | 2/2003 | Ashkenazi | 514/12 |
| 2003/0049735 | A1 | 3/2003 | Eaton | 435/69.1 |
| 2003/0049752 | A1 | 3/2003 | Baker | 435/69.1 |
| 2003/0049755 | A1 | 3/2003 | Baker | 435/69.1 |
| 2003/0050462 | A1 | 3/2003 | Eaton | 536/23.2 |
| 2003/0050465 | A1 | 3/2003 | Eaton | 536/23.2 |
| 2003/0054359 | A1 | 3/2003 | Ashkenazi | 435/6 |
| 2003/0054403 | A1 | 3/2003 | Ashkenazi | 435/7.1 |
| 2003/0054404 | A1 | 3/2003 | Ashkenazi | 435/7.1 |
| 2003/0054472 | A1 | 3/2003 | Baker | 435/69.1 |
| 2003/0054987 | A1 | 3/2003 | Ashkenazi | 514/12 |
| 2003/0055222 | A1 | 3/2003 | Eaton | 530/388.1 |
| 2003/0055224 | A1 | 3/2003 | Gao | 530/388.26 |
| 2003/0059780 | A1 | 3/2003 | Ashkenazi | 435/6 |
| 2003/0059782 | A1 | 3/2003 | Ashkenazi | 435/6 |
| 2003/0059783 | A1 | 3/2003 | Ashkenazi | 435/6 |
| 2003/0059832 | A1 | 3/2003 | Ashkenazi | 435/7.1 |
| 2003/0059833 | A1 | 3/2003 | Ashkenazi | 435/7.1 |
| 2003/0060407 | A1 | 3/2003 | Ashkenazi | 514/12 |
| 2003/0060600 | A1 | 3/2003 | Eaton | 530/350 |
| 2003/0065161 | A1 | 4/2003 | Eaton | 536/23.5 |
| 2003/0068623 | A1 | 4/2003 | Ashkenazi | 435/6 |
| 2003/0068680 | A1 | 4/2003 | Baker | 435/69.1 |
| 2003/0068708 | A1 | 4/2003 | Baker | 435/69.1 |
| 2003/0068713 | A1 | 4/2003 | Baker | 435/69.1 |
| 2003/0068761 | A1 | 4/2003 | Baker | 435/69.1 |
| 2003/0068762 | A1 | 4/2003 | Baker | 435/69.1 |
| 2003/0068771 | A1 | 4/2003 | Baker | 435/69.1 |
| 2003/0069394 | A1 | 4/2003 | Baker | 530/350 |
| 2003/0073090 | A1 | 4/2003 | Ashkenazi | 435/6 |
| 2003/0073173 | A1 | 4/2003 | Baker | 435/69.1 |
| 2003/0073180 | A1 | 4/2003 | Baker | 435/69.1 |
| 2003/0073181 | A1 | 4/2003 | Baker | 435/69.1 |
| 2003/0082767 | A1 | 5/2003 | Baker | 435/183 |
| 2003/0083461 | A1 | 5/2003 | Ashkenazi | 435/7.1 |
| 2003/0083473 | A1 | 5/2003 | Eaton | 530/388.15 |
| 2003/0087304 | A1 | 5/2003 | Ashkenazi | 435/7.1 |
| 2003/0087305 | A1 | 5/2003 | Ashkenazi | 435/7.1 |
| 2003/0087376 | A1 | 5/2003 | Baker | 435/69.1 |
| 2003/0091580 | A1 | 5/2003 | Mitcham et al. | 424/185.1 |
| 2003/0092121 | A1 | 5/2003 | Baker | 435/69.1 |
| 2003/0211572 | A1 | 11/2003 | Baker | 435/69.1 |
| 2003/0211574 | A1 | 11/2003 | Baker | 435/69.1 |

FOREIGN PATENT DOCUMENTS

| EP | 1033401 A2 | 9/2000 |
|---|---|---|
| JP | 9149790 A | 6/1997 |
| WO | WO97/24435 A1 | 7/1997 |
| WO | WO97/38125 | 10/1997 |
| WO | WO98/14466 A1 | 4/1998 |
| WO | WO98/21331 | 5/1998 |
| WO | WO98/56804 A1 | 12/1998 |
| WO | WO99/25850 | 5/1999 |
| WO | WO99/25877 A1 | 5/1999 |
| WO | WO99/36550 A2 | 7/1999 |

(Continued)

OTHER PUBLICATIONS

Alberts et al. (Molecular Biology of the Cell, 3rd edition, 1994, p. 465).*
Greenbaum et al. (Genome Biology, 2003, vol. 4, Issue 9, pp. 117.1-117.8).*
Christiansen et al (Mol Cancer Ther, 2004, 3:1493-1501).*
Topp et al (Journal of Controlled Release, 1998, 53:15-23).*
Jain (Scientific American Jul. 1994).*
Dillman (Annals of Internal Medicine, vol. 111, pp. 592-603, 1989).*
Weiner (Seminars Oncology, vol. 26, No. 4, 1999, pp. 41-50).*
Choi et al. "Genomic Organization and Expression Analysis of B7-H4, an imn Inhibitory Molecule of the B7 Family" J Immunol 2003 171(9):4650-4654.
Database Genebank, Accession No. US54603, Gress et al., HSU54603 Human pancreatic cancer (Cwallrapp) *Homo sapiens* cDNA clone rda12, mRNA sequence, Nov. 18, 1997.

(Continued)

*Primary Examiner* — Sean Aeder
(74) *Attorney, Agent, or Firm* — Licata & Tyrrell P.C.; Keith McCollum

(57) ABSTRACT

The present invention provides a new method for detecting, diagnosing, monitoring, staging, prognosticating, imaging and treating selected cancers including gynecologic cancers such as breast, ovarian, uterine and endometrial cancer and lung cancer.

2 Claims, No Drawings

FOREIGN PATENT DOCUMENTS

| | | |
|---|---|---|
| WO | WO99/45147 | 9/1999 |
| WO | WO99/63088 A2 | 12/1999 |
| WO | WO00/12708 A2 | 3/2000 |
| WO | WO00/12758 A1 | 3/2000 |
| WO | WO00/18961 | 4/2000 |
| WO | WO00/36107 A2 | 6/2000 |
| WO | WO00/55629 A2 | 9/2000 |
| WO | WO00/55633 A2 | 9/2000 |
| WO | WO00/73454 A1 | 12/2000 |
| WO | WO00/76531 A1 | 12/2000 |
| WO | WO00/78960 A2 | 12/2000 |
| WO | WO00/78961 A1 | 12/2000 |
| WO | WO01/40269 A2 | 6/2001 |
| WO | WO01/94641 A2 | 12/2001 |
| WO | WO02/02587 A1 | 1/2002 |
| WO | WO02/02624 A2 | 1/2002 |
| WO | WO02/06317 A2 | 1/2002 |
| WO | WO02/102235 A2 | 12/2002 |

OTHER PUBLICATIONS

Database Genebank, Accession No. AP000665, Hattori et al., *Homo sapiens* genomic DNA, chromosome 11q clone:CMB9-46G18, complete sequences, Feb. 22, 2001.

Database Genebank, Accession No. AP002800, Hattori et al., *Homo sapiens* genomic DNA, chromosome 11q clone:RP11-832A4, complete sequences, Jul. 18, 2001.

Database Genebank, Accession No. XM_006448, NCBI Annotation Project, *Homo sapiens* transmembrane protease, serine 4 (TMPRSS4), mRNA, Oct. 16, 2001.

Database Genebank, Accession No. NM_005656, Paoloni-Giacobino et al., *Homo sapiens* transmembrane protease, serine 2 (TMPRSS2), mRNA, Jul. 5, 2001.

Database Genebank, Accession No. AF216312, Smeekens et al., *Homo sapiens* type II membrane serine protease mRNA, complete cds, Feb. 7, 2000.

Database Genebank, Accession No. BC011703, Strausberg, R., *Homo sapiens*, Similar to mosaic serine protease, clone MGC:19490 Image:3610695, mRNA, complete cds, Aug. 2, 2001.

Database Genebank, Accession No. AF179224, Wallrapp et al., *Homo sapiens* transmembrane serine protease 3 (TMPRSS3) mRNA, complete cds, Jun. 8, 2000.

el-Shirbiny, A. M. "Prostatic Specific Antigen" Adv. Clin. Chem. 1994 31:99-133 Abstract.

Fu et al. "Translational Regulation of Human p53 Gene Expression" EMBO Journal 1996 15(16):4392-4401.

Gress et al. "Identification of Genes with Specific Expression in Pancreatic Cancer by cDNA Representational Difference Analysis" Genes Chromosomes Cancer 1997 19(2):97-103.

Jaakola et al. "Prostate Cancer, Prostate-Specific Antigen, and the Polymerase Chain Reaction" Clin. Chem. 1995 41(2):177-9 Abstract.

Jang et al. "An Examination of the Effects of Hypoxia, Acidosis, and Glucose Starvation on the Expression of Metastasis-Associated Genes in Murine Tumor Cells" Clin Exp Metastasis 1997 15(5):469-483.

Kozak, M. "An analysis of 5'-noncoding Sequences from 699 Vertebrate Messenger RNAs" Nucleic Acids Res. 1987 15(20):8125-48.

Kozak, M. "An Analysis of Vertebrate mRNA Sequences: Intimations of Translational Control" J Cell Biol 1991 115(4):887-903.

Kozak, M. "Compilation and Analysis of Sequences Upstream from the Translational Start Site in Eukaryotic mRNAs" Nucleic Acids Res. 1984 12(2):857-72.

Kozak, M. "Possible Role of Flanking Nucleotides in Recognition of the AUG Initiator Codon by Eukaryotic Ribosomes" Nucleic Acids Res. 1981 9(20):5233-52.

Lewin et al. Genes VI Oxford University Press 1990 p. 810.

Lopez-Guerrero et al. "Histological Tumor Grade Correlates with HER2/c-erB-2 Status in Invasive Breast Cancer: a Comparative Analysis between Immunohistochemical (CB11 Clone and Herceptest), FISH and Differential PCR Procedures" Arkh. Patol. 2003 65(1):50-5 Abstract.

Misao et al. "Expression of Sex Hormone-Binding Globulin Exon VII Splicing Variant Messenger RNA in Human Uterine Endometrial Cancers" Cancer Research 1997 57:5579-5583.

NCBI Genbank Accession No. AK026071 [gi:10438801] Sep. 29, 2000 with Revision History.

NCBI Genbank Accession No. NM_024626 [gi:13375849] Mar. 18, 2001 with Revision History.

NCBI Genbank Accession No. NP_078902 [gi:13375850] Mar. 18, 2001-Dec. 10, 2001 with Revision History.

NCBI Genbank Accession No. XP_227553 [gi:27660086] Jan. 13, 2003 with Revision History—The Revision History of 34860049 which replaces 27660086 is provided.

NCBI Genbank Accession No. BC032925 [gi:21410734] Jun. 13, 2002 with Revision History.

NCBI Genbank Accession No. NP_848709 [gi:30519900] May 10, 2003 with Revision History.

NCBI Genbank Accession No. AAP37283 [gi:31322920] Jun. 1, 2003 with Revision History.

NCBI Genbank Accession No. AAP37284 [gi:31322922] Jun. 1, 2003 with Revision History.

NCBI Genbank Accession No. AY280972 [gi:31322919] Jun. 1, 2003 with Revision History.

NCBI Genbank Accession No. AAP88965 [gi:32892037] Jul. 22, 2003 with Revision History.

NCBI Genbank Accession No. AY346100 [gi:33638210] Aug. 19, 2003 with Revision History.

NCBI Genbank Accession No. AY358352 [gi:37181828] Oct. 1, 2003 with Revision History.

NCBI Genbank Accession No. AAH65717 [gi:41350862] Jan. 27, 2004 with Revision History.

Paoloni-Giacobino et al. "Cloning of the TMPRSS2 Gene, which Encodes a Novel Serine Protease with Transmembrane, LDLRA, and SRCR Domains and Maps to 21q22.3" Genomics 1997 44:309-320.

Pennica et al. "WISP Genes Are Members of the Connective Tissue Growth Factor Family that Are Up-Regulated in wnt-1-transformed Cells and Aberrantly Expressed in Human Colon Tumors" PNAS 1998 95(25):14717-14722.

Powell et al. "Expression of Cytochrome P4502E1 in Human Liver: Assessment by mRNA, Genotype and Phenotype" Pharmacogenetics 1998 8(5):411-421.

Prasad et al. "B7S1, a Novel B7 Family Member that Negatively Regulates T cell Immunity" Immunity 2003 18(6):863-873.

Salceda et al. "The Immunomodulatory Protein B7-H4 Is Overexpressed in Breast and Ovarian Cancers and Promotes Epithelial Cell Transformation" Experimental Cell Research 2005 306(1):128-41.

Sica et al. "B7-H4, a Molecule of the B7 Family, Negatively Regulates T Cell Immunity" Immunity 2003 18(6):849-861.

Singer, M. and Berg, P. Genes and Genomes 1991 University Science Books(Mill Valley, CA):180-182.

Straub et al. "Detection of Prostate-Specific Antigen RNA Before and After Radical Retropubic Prostatectomy and Transurethral Resection of the Prostate Using "Light-Cycler"-Based Quantitative Real-Time Polymerase Chain Reaction" Urology 2001 58(5):815-20 Abstract.

Strausberg et al. "Generation and Initial Analysis of More than 15,000 Full-Length Human and Mouse cDNA Sequences" Proc. Natl. Acad. Sci. USA 2002 99(26):16899-16903.

Tringler et al. "B7-h4 is highly expressed in ductal and lobular breast cancer" Clinical Cancer Research 2005 11:1842-1848.

Vallejo et al. "Evidence of Tissue-Specific, Post-Transcriptional Regulation of NRF-2 Expression" Biochimie 2000 82(12):1129-1133.

Wallrapp et al. "A Novel Transmembrane Serine Protease (TMPRSS3) Overexpressed in Pancreatic Cancer" Cancer Research 2000 60(10):2602-2606.

Watson et al. Molecular Biology of the Gene 1987 The Benjamin/Cummings Publishing Company, Inc. (Menlo Park, California):568-569.

Zang et al. "B7x: A Widely Expressed B7 Family Member that Inhibits T Cell Activation" Proc. Natl. Acad. Sci. USA 2003 100(18):10388-10392.

U.S. Appl. No. 08/972,376, filed May 27, 1999, Cohen et al.
U.S. Appl. No. 09/216,003, filed Jun. 22, 2000, Mitcham et al.
U.S. Appl. No. 09/636,801, filed Aug. 10, 2000, Mitcham et al.
U.S. Appl. No. 60/138,625, filed Dec. 21, 2000, Komatsoulis et al.

\* cited by examiner

```
                       SEQUENCE LISTING

<160> NUMBER OF SEQ ID NOS: 16

<210> SEQ ID NO 1
<211> LENGTH: 2587
<212> TYPE: DNA
<213> ORGANISM: Homo sapien

<400> SEQUENCE: 1
ggaaggcagc gggcagctcc actcagccag tacccagata cgctgggaac cttccccagc        60
catggcttcc ctggggcaga tcctcttctg gagcataatt agcatcatca ttattctggc       120
tggagcaatt gcactcatca ttggctttgg tatttcaggg agacactcca tcacagtcac       180
tactgtcgcc tcagctggga acattgggga ggatggaatc ctgagctgca ctttgaacc        240 tgacatcaaa ctttctgata tcgtgataca atggctgaag gaaggtgttt taggcttggt       300
```

```
ccatgagttc aaagaaggca aagatgagct gtcggagcag gatgaaatgt tcagaggccg    360
gacagcagtg tttgctgatc aagtgatagt tggcaatgcc tctttgcggc tgaaaaacgt    420
gcaactcaca gatgctggca cctacaaatg ttatatcatc acttctaaag caaggggaa     480
tgctaacctt gagtataaaa ctggagcctt cagcatgccg gaagtgaatg tggactataa    540
tgccagctca gagaccttgc ggtgtgaggc tccccgatgg ttcccccagc ccacagtggt    600
ctgggcatcc caagttgacc agggagccaa cttctcggaa gtctccaata ccagctttga    660
gctgaactct gagaatgtga ccatgaaggt tgtgtctgtg ctctacaatg ttacgatcaa    720
caacacatac tcctgtatga ttgaaaatga cattgccaaa gcaacagggg atatcaaagt    780
gacagaatcg gagatcaaaa ggcggagtca cctacagctg ctaaaactcaa aggcttctct    840
gtgtgtctct tctttctttg ccatcagctg ggcacttctg cctctcagcc cttacctgat    900
gctaaaataa tgtgccttgg ccacaaaaaa gcatgcaaag tcattgttac aacagggatc    960
tacagaacta tttcaccacc agatatgacc tagttttata tttctgggag gaatgaatt    1020
catatctaga agtctggagt gagcaaacaa gagcaagaaa caaaagaag ccaaaagcag    1080
aaggctccaa tatgaacaag ataaatctat cttcaaagac atattagaag ttgggaaaat    1140
aattcatgtg aactagacaa gtgtgttaag agtgataagt aaaatgcacg tggagacaag    1200
tgcatcccca gatctcaggg acctccccct gcctgtcacc tggggagtga gaggacagga    1260
tagtgcatgt tctttgtctc tgaatttta gttatatgtg ctgtaatgtt gctctgagga    1320
agcccctgga aagtctatcc caacatatcc acatcttata ttccacaaat taagctgtag    1380
tatgtacccct aagacgctgc taattgactg ccacttcgca actcagggc ggctgcattt    1440
tagtaatggg tcaaatgatt cacttttat gatgcttcca aaggtgcctt ggcttctctt    1500
cccaactgac aaatgccaaa gttgagaaaa atgatcataa ttttagcata aacagagcag    1560
tcggcgacac cgattttata aataaactga gcaccttctt tttaaacaaa caaatgcggg    1620
tttatttctc agatgatgtt catccgtgaa tggtccaggg aaggacccttt caccttgact    1680
atatggcatt atgtcatcac aagctctgag gcttctcctt tccatcctgc gtggacagct    1740
aagacctcag ttttcaatag catctagagc agtgggactc agctgggggtg atttcgcccc    1800
ccatctccgg gggaatgtct gaagacaatt ttggttacct caatgaggga gtggaggagg    1860
atacagtgct actaccaact agtggataaa ggccagggat gctgctcaac ctcctaccat    1920
gtacaggacg tctccccatt acaactaccc aatccgaagt gtcaactgtg tcaggactaa    1980
gaaaccctgg ttttgagtag aaaagggcct ggaaagaggg gagccaacaa atctgtctgc    2040
ttctcacatt agtcattggc aaataagcat tctgtctctt tggctgctgc ctcagcacag    2100
agagccagaa ctctatcggg caccaggata acatctctca gtgaacagag ttgacaaggc    2160
ctatgggaaa tgcctgatgg gattatcttc agcttgttga gcttctaagt ttctttccct    2220
tcattctacc ctgcaagcca agttctgtaa gagaaatgcc tgagttctag ctcaggtttt    2280
cttactctga atttagatct ccagacccctt cctggccaca attcaaatta aggcaacaaa    2340
catataccctt ccatgaagca cacacagact tttgaaagca aggacaatga ctgcttgaat    2400
tgaggccttg aggaatgaag ctttgaagga aaagaatact ttgtttccag ccccccttccc    2460
acactcttca tgtgttaacc actgccttcc tggaccttgg agccacggtg actgtattac    2520
atgttgttat agaaaactga ttttagagtt ctgatcgttc aagagaatga ttaaatatac    2580
atttcct                                                              2587
```

```
<210> SEQ ID NO 2
<211> LENGTH: 2070
<212> TYPE: DNA
<213> ORGANISM: Homo sapien

<400> SEQUENCE: 2
cacagagaga ggcagcagct tgctcagcgg acaaggatgc tgggcgtgag ggaccaaggc      60
ctgccctgca ctcgggcctc ctccagccag tgctgaccag ggacttctga cctgctggcc     120
agccaggacc tgtgtgggga ggccctcctg ctgccttggg gtgacaatct cagctccagg     180
ctacagggag accgggagga tcacagagcc agcatgttac aggatcctga cagtgatcaa     240
cctctgaaca gcctcgatgt caaacccctg cgcaaacccc gtatccccat ggagaccttc     300
agaaaggtgg ggatccccat catcatagca ctactgagcc tggcgagtat catcattgtg     360
gttgtcctca tcaaggtgat tctggataaa tactacttcc tctgcgggca gcctctccac     420
ttcatcccga ggaagcagct gtgtgacgga gagctggact gtcccttggg ggaggacgag     480
gagcactgtg tcaagagctt ccccgaaggg cctgcagtgg cagtccgcct ctccaaggac     540
cgatccacac tgcaggtgct ggactcggcc acagggaact ggttctctgc ctgtttcgac     600
aacttcacag aagctctcgc tgagacagcc tgtaggcaga tgggctacag cagcaaaccc     660
actttcagag ctgtggagat tggcccagac caggatctgg atgttgttga aatcacagaa     720
aacagccagg agcttcgcat gcggaactca agtgggccct gtctctcagg ctccctggtc     780
tccctgcact gtcttgcctg tgggaagagc ctgaagaccc ccgtgtggt gggtggggag      840 gaggcctctg tggattcttg gccttggcag gtcagcatcc agtacgacaa acagcacgtc     900
tgtggaggga gcatcctgga cccccactgg gtcctcacgg gcagcccact gcttcaggaa     960
acataccgat gtgttcaact ggaaggtgcg ggcaggctca gacaaactgg gcagcttccc    1020
atccctggct gtggccaaga tcatcatcat tgaattcaac cccatgtacc ccaaagacaa    1080
tgacatcgcc ctcatgaagc tgcagttccc actcactttc tcaggcacag tcaggcccat    1140
ctgtctgccc ttctttgatg aggagctcac tccagccacc ccactctgga tcattggatg    1200
gggctttacg aagcagaatg gagggaagat gtctgacata ctgctgcagg cgtcagtcca    1260
ggtcattgac agcacacggt gcaatgcaga cgatgcgtac cagggggaag tcaccgagaa    1320
gatgatgtgt gcaggcatcc cggaaggggg tgtggacacc tgccagggtg acagtggtgg    1380 gccctgatg taccaatctg accagtggca tgtggtgggc atcgttagct ggggctatgg     1440 ctgcggggc ccgagcaccc caggagtata caccaaggtc tcagcctatc tcaactggat     1500
ctacaatgtc tggaaggctg agctgtaatg ctgctgcccc tttgcagtgc tgggagccgc    1560
ttccttcctg ccctgcccac ctggggatcc cccaaagtca gacacagagc aagagtcccc    1620
ttgggtacac ccctctgccc acagcctcag catttcttgg agcagcaaag ggcctcaatt    1680
cctataagag accctcgcag cccagaggcg cccagaggaa gtcagcagcc ctagctcggc    1740
cacacttggt gctcccagca tcccagggag agacacagcc cactgaacaa ggtctcaggg    1800
gtattgctaa gccaagaagg aactttccca cactactgaa tggaagcagg ctgtcttgta    1860
aaagcccaga tcactgtggg ctggagagga gaaggaaagg gtctgcgcca gcctgtccg     1920 tcttcaccca tccccaagcc tactagcaga agaaaccagt tgtaatataa aatgcactgc    1980
cctactgttg gtatgactac cgttacctac tgttgcattg ttattacagc tatggccact    2040
attattaaag agctgtgtaa catctctggc                                    2070

<210> SEQ ID NO 3
<211> LENGTH: 1709
```

```
<212> TYPE: DNA
<213> ORGANISM: Homo sapien

<400> SEQUENCE: 3
agcagactca caccagaact acattccctg gcccctgcc tgtgtgcttc tggccaggcc      60
ttggttggca agtctgaccc gagaaaagga tctgcagaaa atcagactat gggatcactt    120
tgtttgtgca ttgggaatga cattctttcc cacccagga aaacctttgg gactttcaga     180
gacattgtgg ctagccaacc acatggtcag cctcaaagtt gagaggctca gtaaccctcc    240
tatccctaga gaattccaaa gtgtggatgt aatttaacta gaaagccatt ggtgactatc    300
tgtgatcctc tggaagtatg ctatgttgtg tatatcttgc atccaaagcc agagggaacc    360
acaatgacta gtaaaacggt ggtctcaatg cccacttagc ctctgcctct gaatttgacc    420
atagtggcgt tcagctgata gagcgggaag aagaaatatg catttttat gaaaaaataa     480
atatccaaga aagatgaaa ctaaatggaa aaattgaaat acatctactg aagaaaaga     540
tccaattcct gaaaatgaag attgctgaga agcaaagaca aatttgtgtg acccagaaat    600
tactgccagc caagaggtcc ctggatgccg acctagctgt gctccaaatt cagttttcac    660
agtgtacaga cagaattaaa gacctggaga acagttcgt aaagcctgat ggtgagaata     720
gagctcgctt ccttccaggg aaagatctga ccgaaaaaga aatgatccaa aaattagaca    780
agctggaact acaactggcc aagaaggagg agaagctgct ggagaaggat ttcatctatg    840
agcaggtctc caggctcaca gacaggctct gcagcaaaac tcagggctgc aagcaggaca    900
cactgctctt agccaagaag atgaatggct atcaaagaag gatcaaaaat gcaactgaga    960
aaatgatggc tcttgttgct gagctgtcca tgaaacaagc cctaaccatt gaactccaaa   1020
aggaagtcag ggagaaagaa gacttcatct tcacttgcaa ttccaggata gaaaaaggtc   1080
tgccactcaa taaggaaatt gagaaagaat ggttgaaagt ccttcgagat gaagaaatgc   1140
acgccttggc catcgctgaa aagtctcagg agttcttgga agcagataat cgccagctgc   1200
ccaatggtgt ttacacaact gcagagcagc gtccgaatgc ctacatccca gaagcagatg   1260
ccactcttcc tttgccaaaa ccttatggtg ctttggctcc tttaaaccc agtgaacctg    1320
gagccaatat gaggcacata aggaaacctg ttataaagcc agttgaaatc tgaatatgtg   1380
aacaaatcca ggcctctcaa ggaaaagact tcaaccaggc ttccttgtac ccacaggtga   1440
aaaatgtgag cataatactt ctaatattat tgataagtaa ggtaaccaca attagtcagc   1500
aacagagtac aacagggttt ctatttaccc accaactact ataccttca tgacgttgaa    1560
tgggacatag aactgtccta catttatgtc aaagtatata tttgaatcgc ttatattttc   1620
tttttcactc tttatattga gtacattcca gaaatttgta gtaggcaagg tgctataaaa   1680
atgcactaaa aataaatctg ttctcaatg                                      1709

<210> SEQ ID NO 4
<211> LENGTH: 257
<212> TYPE: DNA
<213> ORGANISM: Homo sapien

<400> SEQUENCE: 4
ttaatgggta agtattttt atatgcttta gctatagcta agaaaactg atacttaaca      60
aagttgaata gtattattca ctggtgctcc taaaatattg tttttcagtg taaaatatgc    120
atatcttcta tatttaatat gaaagtcttg aaatgtatca gacagaaggg gatttcagtt    180
tgcaaataat gagcaatgta gcaattttaa cacatttcat aaatatatat tttgtcattg    240
gtggagagca ccatttg                                                   257
```

<210> SEQ ID NO 5
<211> LENGTH: 359
<212> TYPE: DNA
<213> ORGANISM: Homo sapien

<400> SEQUENCE: 5

| | | | | | | |
|---|---|---|---|---|---|---|
| gcctgagagc | acttagcgtt | catgagtgtc | cccaccatgg | cctggatgat | gcttctcctc | 60 |
| ggactccttg | cttatggatc | aggtcaggga | gtggattctc | agactgtggt | gacccaagag | 120 |
| ccatcgttat | cagtgtcccc | tggagggaca | gtcacactca | cttgtggctt | ggcctctgac | 180 |
| tcagtctcta | ctaatttctt | ccccacctgg | taccagcaga | ccccaggcca | ggctccacgc | 240 |
| acgctcatct | acagcacaag | cactcgctct | ctggggtcc | ctgatcgttt | ctctggctcc | 300 |
| atccttggga | caaagctgc | cctcaccatt | acggggccc | aggcagatga | tgaatctga | 359 |

<210> SEQ ID NO 6
<211> LENGTH: 1372
<212> TYPE: DNA
<213> ORGANISM: Homo sapien
<220> FEATURE:
<221> NAME/KEY: misc_feature
<222> LOCATION: (6)..(6)
<223> OTHER INFORMATION: n = a, c, g or t
<220> FEATURE:
<221> NAME/KEY: misc_feature
<222> LOCATION: (9)..(9)
<223> OTHER INFORMATION: n = a, c, g or t

<400> SEQUENCE: 6

| | | | | | | |
|---|---|---|---|---|---|---|
| ccttanagnc | ttggttgcca | aacagaatgc | ccatatccgt | cttacttgtg | aggaagcttg | 60 |
| ccttgggcgc | cctctgctgg | ccctcctgaa | gctaacaggg | gcgagtgctc | ggtggtttac | 120 |
| aaattgcctc | catgcagact | atgaaactgt | tcagcctgct | atagttagat | ctctggcact | 180 |
| ggcccaggag | gtcttgcaga | tttgcagatc | aaggagaacc | caggagtttc | aaagaagcgg | 240 |
| ctagtaaagg | tctctgagat | ccttgcacta | gctacatcct | cagggtagga | ggaagatggc | 300 |
| ttccagaagc | atgcggctgc | tcctattgct | gagctgcctg | gccaaaacag | gagtcctggg | 360 |
| tgatatcatc | atgagaccca | gctgtgctcc | tgggatggtt | ttaccacaag | tccaattgct | 420 |
| atggttactt | caggaagctg | aggaactggt | ctgatgccga | gctcgagtgt | cagtcttacg | 480 |
| gaaacggagc | ccacctggca | tctatcctga | gtttaaagga | agccagcacc | atagcagagt | 540 |
| acataagtgg | ctatcagaga | agccagccga | tatggattgg | cctgcacgac | ccacagaaga | 600 |
| ggcagcagtg | gcagtggatt | gatggggcca | tgtatctgta | cagatcctgg | tctggcaagt | 660 |
| ccatgggtgg | gaacaagcac | tgtgctgaga | tgagctccaa | taacaacttt | ttaacttgga | 720 |
| gcagcaacga | atgcaacaag | cgccaacact | tcctgtgcaa | gtaccgacca | tagagcaaga | 780 |
| atcaagattc | tgctaactcc | tgcacagccc | cgtcctcttc | ctttctgcta | gcctggctaa | 840 |
| atctgctcat | tatttcagag | gggaaaccta | gcaaactaag | agtgataagg | gccctactac | 900 |
| actggctttt | ttaggcttag | agacagaaac | tttagcattg | gcccagtagt | ggcttctagc | 960 |
| tctaaatgtt | tgccccgcca | tcccttccca | cagtatcctt | cttccctcct | ccctgtctc | 1020 |
| tggctgtctc | gagcagtcta | gaagagtgca | tctccagcct | atgaaacagc | tgggtctttg | 1080 |
| gccataagaa | gtaaagattt | gaagacagaa | ggaagaaact | caggagtaag | cttctagccc | 1140 |
| ccttcagctt | ctacacccctt | ctgccctctc | tccattgcct | gcaccccacc | ccagccactc | 1200 |
| aactcctgct | tgttttcct | ttggccatgg | gaaggtttac | cagtagaatc | cttgctaggt | 1260 |
| tgatgtgggc | catacattcc | tttaataaac | cattgtgtac | ataagaggtt | gctgtgttcc | 1320 |

```
agttcagtaa atggtgaatg tggaaaagtg aaataagacc aagaaataca aa          1372

<210> SEQ ID NO 7
<211> LENGTH: 291
<212> TYPE: DNA
<213> ORGANISM: Homo sapien
<220> FEATURE:
<221> NAME/KEY: misc_feature
<222> LOCATION: (277)..(277)
<223> OTHER INFORMATION: n= a, c, g, or t

<400> SEQUENCE: 7
agaatggtag tagtaagaag aagaaaaata gaggatctga atgtattttg aaggtagagt    60
ccactggact tagagatgga ttgaatgtgg aagattaagg aaagggagaa atgaaagata   120
gtcttaggtt tcatcttcag atgactgggt gaacagcagt gttctttgct aagatgggga   180
agactaggga aaagagccag ttctgtattg agcatattat atttaagaca atcccatctg   240
ggtccaaaga caatgttgat tttttttctt agatacntgc cctttagacc t            291

<210> SEQ ID NO 8
<211> LENGTH: 1275
<212> TYPE: DNA
<213> ORGANISM: Homo sapien
<220> FEATURE:
<221> NAME/KEY: misc_feature
<222> LOCATION: (410)..(410)
<223> OTHER INFORMATION: n= a, c, g, or t
<220> FEATURE:
<221> NAME/KEY: misc_feature
<222> LOCATION: (728)..(756)
<223> OTHER INFORMATION: n= a, c, g, or t
<220> FEATURE:
<221> NAME/KEY: misc_feature
<222> LOCATION: (957)..(957)
<223> OTHER INFORMATION: n= a, c, g, or t

<400> SEQUENCE: 8
attctagaac atatgtataa gctaaaaaca gtattttact cagatcagta gttatcgtgt    60
ctatcagcta taaaaaaaat caactgccag ccaagaactt taaaacttta agctgtgtat   120
tatagaaccg ttttgtgtag cattggaata ttgtccattt tgtaagtcat tgtgaatgtt   180
cttaattatc agcttgaagg tattttttgta ttaaaagttg acattgaaga acctaagtgg   240
atgatgggat ttggggccag tagtgaaagt atgtttcctc taaaatattt ccctaaacag   300
tggtatacat ggttatttta ttatgagatt tgtatatgtt ctgtgtttct ctgtgaacaa   360
tgtttcagtc tctctgtcac catatgtaag gggaagtcca caaatatagn actacattgc   420
acaaaactaa aattgttaat tacaagaaaa tataggtgct tacctttga aggtttatta   480 atacatatgg ttgtcacaat acgtatatat gataaatggt gtacatatac agatgtttat   540
ggtgtataaa ttttctata cccaattaga attatcttcc tgattcttta ttcaataaca   600
tgctaattcc tcttctatgt tctatagtga cagaatgcta acttttctta taccctggca   660
gaggacagag gagtctggtc taggatgggg aactgaattt ttgaacgaaa aggaaagaga   720
aaggatgnnn nnnnnnnnn nnnnnnnnnn nnnnntaat gtttcttagt cattttgatt   780
ggccatttga acagtctaca agtttaacgt tatttccagt gaagtaggat ggctgaccta   840
gcaatacatg tttcttcaaa agggtaaaca tgctttagtg acctaaagct aaattttgta   900
catttgacat caggggtgtt ataagtactg cacttaatac aaagctattt ctcaatngtg   960 ttattttga gacaaatttt tcttcaccat taacttcttg ttggtagctt tttgttttgt  1020
aaaaattgag agatggcaat gcttatctca accagattat ccatctgcag aattaaggta  1080
```

| | |
|---|---:|
| tgcaactggt aaataaaaga caaatgctcc agtttgtctt tctcaacctt tgagttctta | 1140 |
| acctttgagt taaaacctag tctaaatagt gggaatgtct tggtttacag taaggttttc | 1200 |
| ttgggaagga tcttggtttt gtgatctatt tgtgaattaa ggagtagatg ttaaccatta | 1260 |
| ttttatagat aagtg | 1275 |

<210> SEQ ID NO 9
<211> LENGTH: 2479
<212> TYPE: DNA
<213> ORGANISM: Homo sapien

<400> SEQUENCE: 9

| | |
|---|---:|
| gtcatattga acattccaga tacctatcat tactcgatgc tgttgataac agcaagatgg | 60 |
| ctttgaactc agggtcacca ccagctattg gaccttacta tgaaaaccat ggataccaac | 120 |
| cggaaaaccc ctatcccgca cagcccactg tggtccccac tgtctacgag gtgcatccgg | 180 |
| ctcagtacta cccgtccccc gtgccccagt acgcccgag gtcctgacg caggcttcca | 240 |
| accccgtcgt ctgcacgcag cccaaatccc catccgggac agtgtgcacc tcaaagacta | 300 |
| agaaagcact gtgcatcacc ttgacccctgg ggaccttcct cgtgggagct cgctggccg | 360 |
| ctggcctact ctggaagttc atgggcagca agtgctccaa ctctgggata gagtgcgact | 420 |
| cctcaggtac ctgcatcaac ccctctaact ggtgtgatgg cgtgtcacac tgccccggcg | 480 |
| gggaggacga gaatcggtgt gttcgcctct acggaccaaa cttcatcctt cagatgtact | 540 |
| catctcagag gaagtcctgg caccctgtgt gccaagacga ctggaacgag aactacgggc | 600 |
| gggcggcctg cagggacatg ggctataaga ataattttta ctctagccaa ggaatagtgg | 660 |
| atgacagcgg atccaccagc tttatgaaac tgaacacaag tgccggcaat gtcgatatct | 720 |
| ataaaaaact gtaccacagt gatgcctgtt cttcaaaagc agtggtttct ttacgctgtt | 780 |
| tagcctgcgg ggtcaacttg aactcaagcc gccagagcag gatcgtgggc ggtgagagcg | 840 |
| cgctcccggg ggcctggccc tggcaggtca gcctgcacgt ccagaacgtc cacgtgtgcg | 900 |
| gaggctccat catcacccc gagtggatcg tgacagccgc ccactgcgtg aaaaacctc | 960 |
| ttaacaatcc atggcattgg acggcatttg cggggatttt gagacaatct ttcatgttct | 1020 |
| atggagccgg ataccaagta caaaaagtga tttctcatcc aaattatgac tccaagacca | 1080 |
| agaacaatga cattgcgctg atgaagctgc agaagcctct gactttcaac gacctagtga | 1140 |
| aaccagtgtg tctgcccaac ccaggcatga tgctgcagcc agaacagctc tgctggattt | 1200 |
| ccgggtgggg ggccaccgag gagaaaggga gacctcaga agtgctgaac gctgccaagg | 1260 |
| tgcttctcat tgagacacag agatgcaaca gcagatatgt ctatgacaac ctgatcacac | 1320 |
| cagccatgat ctgtgccggc ttcctgcagg ggaacgtcga ttcttgccag ggtgacagtg | 1380 |
| gagggcctct ggtcacttcg aacaacaata tctggtggct gataggggat acaagctggg | 1440 |
| gttctggctg tgccaaagct tacagaccag gagtgtacgg gaatgtgatg gtattcacgg | 1500 |
| actggattta tcgacaaatg aaggcaaacg gctaatccac atggtcttcg tccttgacgt | 1560 |
| cgttttacaa gaaaacaatg gggctggttt tgcttccccg tgcatgattt actcttagag | 1620 |
| atgattcaga ggtcacttca ttttattaa acagtgaact tgtctggctt tggcactctc | 1680 |
| tgccatactg tgcaggctgc agtggctccc ctgcccagcc tgctctccct aacccttgt | 1740 |
| ccgcaagggg tgatgccgg ctggttgtgg gcactggcgg tcaattgtgg aaggaagagg | 1800 |
| gttggaggct gccccattg agatcttcct gctgagtcct ttccagggc caattttgga | 1860 |
| tgagcatgga gctgtcactt ctcagctgct ggatgacttg agatgaaaaa ggagagacat | 1920 |

| | |
|---|---|
| ggaaagggag acagccaggt ggcacctgca gcggctgccc tctggggcca cttggtagtg | 1980 |
| tccccagcct acttcacaag gggatttttgc tgatgggttc ttagagcctt agcagccctg | 2040 |
| gatggtggcc agaaataaag ggaccagccc ttcatgggtg gtgacgtggt agtcacttgt | 2100 |
| aaggggaaca gaaacatttt tgttcttatg gggtgagaat atagacagtg cccttggtgc | 2160 |
| gagggaagca attgaaaagg aacttgccct gagcactcct ggtgcaggtc tccacctgca | 2220 |
| cattgggtgg ggctcctggg agggagactc agccttcctc ctcatcctcc ctgaccctgc | 2280 |
| tcctagcacc ctggagagtg aatgccccett ggtccctggc agggcgccaa gtttggcacc | 2340 |
| atgtcggcct cttcaggcct gatagtcatt ggaaattgag gtccatgggg gaaatcaagg | 2400 |
| atgctcagtt taaggtacac tgtttccatg ttatgtttct acacattgat ggtggtgacc | 2460 |
| ctgagttcaa agccatctt | 2479 |

<210> SEQ ID NO 10
<211> LENGTH: 576
<212> TYPE: DNA
<213> ORGANISM: Homo sapien

<400> SEQUENCE: 10

| | |
|---|---|
| ttcaaagaca tattagaagt tgggaaaata attcatgtga actagacaag tgtgttaaga | 60 |
| gtgataagta aaatgcacgt ggagacaagt gcatccccag atctcaggga cctcccctg | 120 |
| cctgtcacct ggggagtgag aggacaggat agtgcatgtt cttgtctct gaattttttag | 180 |
| ttatatgtgc tgtaatgttg ctctgaggaa gccctggaa agtctatccc aacatatcca | 240 |
| catcttatat tccacaaatt aagctgtagt atgtaccctta agacgctgct aattgactgc | 300 |
| cacttcgcaa ctcaggggcg gctgcatttt agtaatgggt caaatgattc actttttatg | 360 |
| atgcttccaa aggtgccttg gcttctcttc ccaactgaca aatgccaaag ttgagaaaaa | 420 |
| tgatcataat tttagcataa acagagcagt cggcgacacc gattttataa ataaactgag | 480 |
| caccttcttt ttaaacaaac aaatgcgggt ttatttctca gatgatgttc atccgtgaat | 540 |
| ggtccaggga aggacctttc accttgacta tatggc | 576 |

<210> SEQ ID NO 11
<211> LENGTH: 890
<212> TYPE: DNA
<213> ORGANISM: Homo sapien

<400> SEQUENCE: 11

| | |
|---|---|
| caagctctga ggcttctcct ttccatcctg cgtggacagc taagacctca gttttcaata | 60 |
| gcatctagag cagtgggact cagctggggt gatttcgccc cccatctccg ggggaatgtc | 120 |
| tgaagacaat tttggttacc tcaatgaggg agtggaggag gatacagtgc tactaccaac | 180 |
| tagtggataa aggccaggga tgctgctcaa cctcctacca tgtacaggga cgtctcccca | 240 |
| ttacaactac ccaatccgaa gtgtcaactg tgtcaggact aagaaaccct ggttttgagt | 300 |
| agaaaagggc ctggaaagag gggagccaac aaatctgtct gcttcctcac attagtcatt | 360 |
| ggcaaataag cattctgtct cttttggctgc tgcctcagca cagagagcca gaactctatc | 420 |
| gggcaccagg ataacatctc tcagtgaaca gagttgacaa ggcctatggg aaatgcctga | 480 |
| tgggattatc ttcagcttgt tgagcttcta agtttctttc ccttcattct accctgcaag | 540 |
| ccaagttctg taagagaaat gcctgagttc tagctcaggt tttcttactc tgaatttaga | 600 |
| tctccagacc cttcctggcc acaattcaaa ttaaggcaac aaacatatac cttccatgaa | 660 |
| gcacacacag acttttgaaa gcaaggacaa tgactgcttg aattgaggcc ttgaggaatg | 720 |

```
aagctttgaa ggaaaagaat actttgtttc cagcccccctt cccacactct tcatgtgtta      780
accactgcct tcctggacct tggagccacg gtgactgtat tacatgttgt tatagaaaac      840
tgattttaga gttctgatcg ttcaagagaa tgattaaata tacatttcct                890
```

<210> SEQ ID NO 12
<211> LENGTH: 406
<212> TYPE: DNA
<213> ORGANISM: Homo sapien
<220> FEATURE:
<221> NAME/KEY: misc_feature
<222> LOCATION: (30)..(30)
<223> OTHER INFORMATION: n= a, c, g, or t
<220> FEATURE:
<221> NAME/KEY: misc_feature
<222> LOCATION: (248)..(248)
<223> OTHER INFORMATION: n= a, c, g, or t
<220> FEATURE:
<221> NAME/KEY: misc_feature
<222> LOCATION: (383)..(383)
<223> OTHER INFORMATION: n= a, c, g, or t

<400> SEQUENCE: 12

```
gtgaatgtgg actataatgc cagctcagan accttgcggt gtgaggctcc ccgatggttc       60
ccccagccca cagtggtctg ggcatcccaa gttgaccagg gagccaactt ctcggaagtc      120
tccaatacca gctttgagct gaactctgag aatgtgacca tgaaggttgt gtctgtgctc      180
tacaatgtta cgatcaacaa cacatactcc tgtatgattg aaaatgacat tgccaaagca      240
acaggggnta tcaaagtgac agaatcggag atcaaaaggc ggagtcacct acagctgcta      300
aactcaaagg cttctctgtg tgtctcttct ttctttgcca tcagctgggc acttctgcct      360 ctcagcccctt acctgatgct aanataatgt gccttggcca caaaaa                    406
```

<210> SEQ ID NO 13
<211> LENGTH: 462
<212> TYPE: DNA
<213> ORGANISM: Homo sapien

<400> SEQUENCE: 13

```
ggaaggcagc ggcagctcca ctcagccagt acccagatac gctgggaacc ttccccagcc       60
atggcttccc tggggcagat cctcttctgg agcataatta gcatcatcat tattctggct      120
ggagcaattg cactcatcat tggctttggt atttcaggga cactccat cacagtcact        180 actgtcgcct cagctgggaa cattggggag atggaatcc tgagctgcac ttttgaacct      240
gacatcaaac tttctgatat cgtgatacaa tggctgaagg aaggtgtttt aggcttggtc      300
catgagttca agaaggcaa agatgagctg tcggagcagg atgaaatgtt cagaggccgg      360
acagcagtgt ttgctgatca agtgatagtt ggcaatgcct ctttgcggct gaaaaacgtg      420
caactcacag atgctggcac ctacaaatgt tatatcatca ct                         462
```

<210> SEQ ID NO 14
<211> LENGTH: 272
<212> TYPE: DNA
<213> ORGANISM: Homo sapien

<400> SEQUENCE: 14

```
gcagcttgct cagcggacaa ggatgctggg cgtgagggac caaggcctgc cctgcactcg       60
ggcctcctcc agccagtgct gaccagggac ttctgacctg ctggccagcc aggacctgtg      120
tggggaggcc ctcctgctgc cttggggtga caatctcagc tccaggctac agggagaccg      180
ggaggatcac agagccagca tggatcctga cagtgatcaa cctctgaaca gcctcgtcaa      240
```
ggtgattctg gataaatact acttcctctg cg					272

<210> SEQ ID NO 15
<211> LENGTH: 492
<212> TYPE: PRT
<213> ORGANISM: Homo sapien

<400> SEQUENCE: 15

Met Ala Leu Asn Ser Gly Ser Pro Ala Ile Gly Pro Tyr Tyr Glu
1               5                   10                  15

Asn His Gly Tyr Gln Pro Glu Asn Pro Tyr Pro Ala Gln Pro Thr Val
            20                  25                  30

Val Pro Thr Val Tyr Glu Val His Pro Ala Gln Tyr Tyr Pro Ser Pro
            35                  40                  45

Val Pro Gln Tyr Ala Pro Arg Val Leu Thr Gln Ala Ser Asn Pro Val
        50                  55                  60

Val Cys Thr Gln Pro Lys Ser Pro Ser Gly Thr Val Cys Thr Ser Lys
65                  70                  75                  80

Thr Lys Lys Ala Leu Cys Ile Thr Leu Thr Leu Gly Thr Phe Leu Val
                85                  90                  95

Gly Ala Ala Leu Ala Ala Gly Leu Leu Trp Lys Phe Met Gly Ser Lys
            100                 105                 110

Cys Ser Asn Ser Gly Ile Glu Cys Asp Ser Ser Gly Thr Cys Ile Asn
            115                 120                 125

Pro Ser Asn Trp Cys Asp Gly Val Ser His Cys Pro Gly Gly Glu Asp
        130                 135                 140

Glu Asn Arg Cys Val Arg Leu Tyr Gly Pro Asn Phe Ile Leu Gln Met
145                 150                 155                 160

Tyr Ser Ser Gln Arg Lys Ser Trp His Pro Val Cys Gln Asp Asp Trp
                165                 170                 175

Asn Glu Asn Tyr Gly Arg Ala Ala Cys Arg Asp Met Gly Tyr Lys Asn
            180                 185                 190

Asn Phe Tyr Ser Ser Gln Gly Ile Val Asp Asp Ser Gly Ser Thr Ser
            195                 200                 205

Phe Met Lys Leu Asn Thr Ser Ala Gly Asn Val Asp Ile Tyr Lys Lys
        210                 215                 220

Leu Tyr His Ser Asp Ala Cys Ser Ser Lys Ala Val Val Ser Leu Arg
225                 230                 235                 240

Cys Leu Ala Cys Gly Val Asn Leu Asn Ser Ser Arg Gln Ser Arg Ile
                245                 250                 255

Val Gly Gly Glu Ser Ala Leu Pro Gly Ala Trp Pro Trp Gln Val Ser
            260                 265                 270

Leu His Val Gln Asn Val His Val Cys Gly Gly Ser Ile Ile Thr Pro
            275                 280                 285

Glu Trp Ile Val Thr Ala Ala His Cys Val Glu Lys Pro Leu Asn Asn
        290                 295                 300

Pro Trp His Trp Thr Ala Phe Ala Gly Ile Leu Arg Gln Ser Phe Met
305                 310                 315                 320

Phe Tyr Gly Ala Gly Tyr Gln Val Gln Lys Val Ile Ser His Pro Asn
                325                 330                 335

Tyr Asp Ser Lys Thr Lys Asn Asn Asp Ile Ala Leu Met Lys Leu Gln
            340                 345                 350

Lys Pro Leu Thr Phe Asn Asp Leu Val Lys Pro Val Cys Leu Pro Asn
        355                 360                 365

```
Pro Gly Met Met Leu Gln Pro Glu Gln Leu Cys Trp Ile Ser Gly Trp
    370                 375                 380

Gly Ala Thr Glu Glu Lys Gly Lys Thr Ser Glu Val Leu Asn Ala Ala
385                 390                 395                 400

Lys Val Leu Leu Ile Glu Thr Gln Arg Cys Asn Ser Arg Tyr Val Tyr
                405                 410                 415

Asp Asn Leu Ile Thr Pro Ala Met Ile Cys Ala Gly Phe Leu Gln Gly
                420                 425                 430

Asn Val Asp Ser Cys Gln Gly Asp Ser Gly Gly Pro Leu Val Thr Ser
            435                 440                 445

Asn Asn Asn Ile Trp Trp Leu Ile Gly Asp Thr Ser Trp Gly Ser Gly
                450                 455                 460

Cys Ala Lys Ala Tyr Arg Pro Gly Val Tyr Gly Asn Val Met Val Phe
465                 470                 475                 480

Thr Asp Trp Ile Tyr Arg Gln Met Lys Ala Asn Gly
                485                 490

<210> SEQ ID NO 16
<211> LENGTH: 890
<212> TYPE: DNA
<213> ORGANISM: Homo sapien
<220> FEATURE:
<221> NAME/KEY: misc_feature
<222> LOCATION: (168)..(237)
<223> OTHER INFORMATION: n=a, c, g or t

<400> SEQUENCE: 16
caagctctga ggcttctcct ttccatcctg cgtggacagc taagacctca gttttcaata        60
gcatctagag cagtgggact cagctggggt gatttcgccc cccatctccg ggggaatgtc       120
tgaagacaat tttggttacc tcaatgaggg agtggaggag gatacagnnn nnnnnnnnnn       180
nnnnnnnnnn nnnnnnnnnn nnnnnnnnnn nnnnnnnnnn nnnnnnnnnn nnnnnnncat       240
tacaactacc caatccgaag tgtcaactgt gtcaggacta agaaaccctg gttttgagta       300
gaaaagggcc tgggaaagag gggagccaac aaatctgtct gcttcctcac attagtcatt       360
ggcaaataag cattctgtct ctttggctgc tgcctcagca cagagagcca gaactctatc       420
gggcaccagg ataacatctc tcagtgaaca gagttgacaa ggcctatggg aaatgcctga       480
tgggattatc ttcagcttgt tgagcttcta agtttctttc ccttcattct accctgcaag       540
ccaagttctg taagagaaat gcctgagttc tagctcaggt tttcttactc tgaatttaga       600
tctccagacc ctgcctggcc acaattcaaa ttaaggcaac aaacatatac cttccatgaa       660
gcacacacag acttttgaaa gcaaggacaa tgactgcttg aattgaggcc ttgaggaatg       720
aagctttgaa ggaaaagaat actttgtttc cagccccctt cccacactct tcatgtgtta       780
accactgcct tcctggacct tggagccacg gtgactgtat tacatgttgt tatagaaaac       840 tgatttaga gttctgatcg ttcaagagaa tgattaaata tacatttcct                   890
```

METHOD OF DIAGNOSING, MONITORING, STAGING, IMAGING AND TREATING VARIOUS CANCERS

INTRODUCTION

This application is a continuation of U.S. application Ser. No. 09/763,978 filed Apr. 25, 2001, now U.S. Pat. No. 7,737,255 which is the U.S. National Phase of PCT/US1999/019655 filed Sep. 1, 1999, which claims the benefit of priority from U.S. Provisional Application Ser. No. 60/098,880 filed Sep. 2, 1998, each of which are herein incorporated by reference in their entireties.

FIELD OF THE INVENTION

This invention relates, in part, to newly developed assays for detecting, diagnosing, monitoring, staging, prognosticating, imaging and treating various cancers, particularly gynecologic cancer including ovarian, uterine endometrial and breast cancer, and lung cancer.

BACKGROUND OF THE INVENTION

The American Cancer Society has estimated that over 560,000 Americans will die this year from cancer. Cancer is the second leading cause of death in the United States, exceeded only by heart disease. It has been estimated that over one million new cancer cases will be diagnosed in 1999 alone.

In women, gynecologic cancers account for more than one-fourth of the malignancies.

Of the gynecologic cancers, breast cancer is the most common. According to the Women's Cancer Network, 1 out of every 8 women in the United States is as risk of developing breast cancer, and 1 out of every 28 women are at risk of dying from breast cancer. Approximately 77% of women diagnosed with breast cancer are over the age of 50. However, breast cancer is the leading cause of death in women between the ages of 40 and 55.

Carcinoma of the ovary is another very common gynecologic cancer. Approximately one in 70 women will develop ovarian cancer during her lifetime. An estimated 14,500 deaths in 1995 resulted from ovarian cancer. It causes more deaths than any other cancer of the female reproductive system. Ovarian cancer often does not cause any noticeable symptoms. Some possible warning signals, however, are an enlarged abdomen due to an accumulation of fluid or vague digestive disturbances (discomfort, gas or distention) in women over 40; rarely there will be abnormal vaginal bleeding. Periodic, complete pelvic examinations are important; a Pap test does not detect ovarian cancer. Annual pelvic exams are recommended for women over 40.

Also common in women is endometrial cancer or carcinoma of the lining of the uterus. According to the Women's Cancer Center endometrial cancer accounts for approximately 13% of all malignancies in women. There are about 34,000 cases of endometrial cancer diagnosed in the United States each year.

Uterine sarcoma is another type of uterine malignancy much more rare as compared to other gynecologic cancers. In uterine sarcoma, malignant cells start growing in the muscles or other supporting tissues of the uterus. Sarcoma of the uterus is different from cancer of the endometrium, a disease in which cancer cells start growing in the lining of the uterus. This uterine cancer usually begins after menopause. Women who have received therapy with high-dose X-rays (external beam radiation therapy) to their pelvis are at a higher risk to develop sarcoma of the uterus. These X-rays are sometimes given to women to stop bleeding from the uterus. Lung cancer is the second most prevalent type of cancer for both men and women in the United States and is the most common cause of cancer death in both sexes. Lung cancer can result from a primary tumor originating in the lung or a secondary tumor which has spread from another organ such as the bowel or breast. Primary lung cancer is divided into three main types; small cell lung cancer; non-small cell lung cancer; and mesothelioma. Small cell lung cancer is also called "Oat Cell" lung cancer because the cancer cells are a distinctive oat shape. There are three types of non-small cell lung cancer. These are grouped together because they behave in a similar way and respond to treatment differently to small cell lung cancer. The three types are squamous cell carcinoma, adenocarcinoma, and large cell carcinoma. Squamous cell cancer is the most common type of lung cancer. It develops from the cells that line the airways. Adenocarcinoma also develops from the cells that line the airways. However, adenocarcinoma develops from a particular type of cell that produces mucus (phlegm). Large cell lung cancer has been thus named because the cells look large and rounded when they are viewed under a microscope. Mesothelioma is a rare type of cancer which affects the covering of the lung called the pleura. Mesothelioma is often caused by exposure to asbestos.

Procedures used for detecting, diagnosing, monitoring, staging, and prognosticating each of these types of cancer are of critical importance to the outcome of the patient. In all cases, patients diagnosed early in development of the cancer generally have a much greater five-year survival rate as compared to the survival rate for patients diagnosed with a cancer which has metastasized. New diagnostic methods which are more sensitive and specific for early detection of various types of cancer are clearly needed.

In the present invention methods are provided for detecting, diagnosing, monitoring, staging, prognosticating, in vivo imaging and treating selected cancers including, but not limited to, gynecologic cancers such as ovarian, breast endometrial and/or uterine cancer, and lung cancer via detection of a Cancer Specific Genes (CSGs). Nine CGSs have been identified and refer, among other things, to native proteins expressed by the genes comprising the polynucleotide sequences of any of SEQ ID NO: 1, 2, 3, 4, 5, 6, 7, 8 or 9. In the alternative, what is meant by the nine CSGs as used herein, means the native mRNAs encoded by the genes comprising any of the polynucleotide sequences of SEQ ID NO: 1, 2, 3, 4, 5, 6, 7, 8 or 9 or it can refer to the actual genes comprising any of the polynucleotide sequences of SEQ ID NO: 1, 2, 3, 4, 5, 6, 7, 8 or 9. Fragments of the CSGs such as those depicted in SEQ ID NO:10, 11, 12, 13 or 14 can also be detected.

Other objects, features, advantages and aspects of the present invention will become apparent to those of skill in the art from the following description. It should be understood, however, that the following description and the specific examples, while indicating preferred embodiments of the invention are given by way of illustration only. Various changes and modifications within the spirit and scope of the disclosed invention will become readily apparent to those skilled in the art from reading the following description and from reading the other parts of the present disclosure.

SUMMARY OF THE INVENTION

Toward these ends, and others, it is an object of the present invention to provide a method for diagnosing the presence of selected cancers by analyzing for changes in levels of CSG in cells, tissues or bodily fluids compared with levels of CSG in preferably the same cells, tissues, or bodily fluid type of a normal human control, wherein a change in levels of CSG in the patient versus the normal human control is associated with the selected cancer. For the purposes of this invention, by "selected cancer" it is meant to include gynecologic cancers such as ovarian, breast, endometrial and uterine cancer, and lung cancer.

Further provided is a method of diagnosing metastatic cancer in a patient having a selected cancer which is not known to have metastasized by identifying a human patient suspected of having a selected cancer that has metastasized; analyzing a sample of cells, tissues, or bodily fluid from such patient for CSG; comparing the CSG levels in such cells, tissues, or bodily fluid with levels of CSG in preferably the same cells, tissues, or bodily fluid type of a normal human control, wherein an increase in CSG levels in the patient versus the normal human control is associated with a cancer which has metastasized.

Also provided by the invention is a method of staging selected cancers in a human patient by identifying a human patient having such cancer; analyzing a sample of cells, tissues, or bodily fluid from such patient for CSG; comparing CSG levels in such cells, tissues, or bodily fluid with levels of CSG in preferably the same cells, tissues, or bodily fluid type of a normal human control sample, wherein an increase in CSG levels in the patient versus the normal human control is associated with a cancer which is progressing and a decrease in the levels of CSG is associated with a cancer which is regressing or in remission.

Further provided is a method of monitoring selected cancers in patients for the onset of metastasis. The method comprises identifying a human patient having a selected cancer that is not known to have metastasized; periodically analyzing a sample of cells, tissues, or bodily fluid from such patient for CSG; comparing the CSG levels in such cells, tissues, or bodily fluid with levels of CSG in preferably the same cells, tissues, or bodily fluid type of a normal human control sample, wherein an increase in CSG levels in the patient versus the normal human control is associated with a cancer which has metastasized.

Further provided is a method of monitoring the change in stage of selected cancers in humans having such cancer by looking at levels of CSG. The method comprises identifying a human patient having a selected cancer; periodically analyzing a sample of cells, tissues, or bodily fluid from such patient for CSG; comparing the CSG levels in such cells, tissue, or bodily fluid with levels of CSG in preferably the same cells, tissues, or bodily fluid type of a normal human control sample, wherein an increase in CSG levels in the patient versus the normal human control is associated with a cancer which is progressing and a decrease in the levels of CSG is associated with a cancer which is regressing or in remission.

Further provided are antibodies against CSG or fragments of such antibodies which can be used to detect or image localization of CSG in a patient for the purpose of detecting or diagnosing selected cancers. Such antibodies can be polyclonal or monoclonal, or prepared by molecular biology techniques. The term "antibody", as used herein and throughout the instant specification is also meant to include aptamers and single-stranded oligonucleotides such as those derived from an in vitro evolution protocol referred to as SELEX and well known to those skilled in the art. Antibodies can be labeled with a variety of detectable labels including, but not limited to, radioisotopes and paramagnetic metals. These antibodies or fragments thereof can also be used as therapeutic agents in the treatment of diseases characterized by expression of a CSG. In therapeutic applications, the antibody can be used without or with derivatization to a cytotoxic agent such as a radioisotope, enzyme, toxin, drug or a prodrug.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

DETAILED DESCRIPTION OF THE INVENTION

The present invention relates to diagnostic assays and methods, both quantitative and qualitative for detecting, diagnosing, monitoring, staging and prognosticating selected cancers by comparing levels of CSG with those of CSG in a normal human control. What is meant by levels of CSG as used herein is levels of the native protein expressed by the gene comprising the polynucleotide sequence of any of SEQ ID NO: 1, 2, 3, 4, 5, 6, 7, 8 or 9. In the alternative, what is meant by levels of CSG as used herein is levels of the native mRNA encoded by the gene comprising any of the polynucleotide sequence of SEQ ID NO: 1, 2, 3, 4, 5, 6, 7, 8 or 9 or levels of the gene comprising any of the polynucleotide sequences of SEQ ID NO:1, 2, 3, 4, 5, 6, 7, 8 or 9. Fragments of CSGs such as those depicted in SEQ ID NO: 10, 11, 12, 13 and 14 can also be detected. Such levels are preferably measured in at least one of cells, tissues and/or bodily fluids, including determination of normal and abnormal levels. Thus, for instance, a diagnostic assay in accordance with the invention for diagnosing over-expression of CSG protein compared to normal control bodily fluids, cells, or tissue samples may be used to diagnose the presence of selected cancers. What is meant by "selected cancers" as used herein is a gynecologic cancer such as ovarian, breast, endometrial or uterine cancer, or lung case.

Any of the 9 CSGs can be measured alone in the methods of the invention, or all together or any combination thereof. However, for methods relating to gynecologic cancers including ovarian, breast, endometrial and uterine cancer, it is preferred that levels of CSG comprising SEQ ID NO:1 or a fragment thereof be determined. Exemplary fragments of this CSG which can be detected are depicted in SEQ ID NO: 10, 11, 12, and 13. For methods relating to lung cancer and gynecologic cancers including ovarian, endometrial and uterine, it is preferred that levels of CSG comprising SEQ ID NO:2 or 9 be determined. Fragments of this CSG such as that depicted in SEQ ID NO:14 can also be detected. For methods relating to ovarian cancer, determination of levels of CSG comprising SEQ ID NO:3 is also preferred.

All the methods of the present invention may optionally include measuring the levels of other cancer markers as well as CSG. Other cancer markers, in addition to CSG, useful in the present invention will depend on the cancer being tested and are known to those of skill in the art.

Diagnostic Assays

The present invention provides methods for diagnosing the presence of selected cancers by analyzing for changes in levels of CSG in cells, tissues or bodily fluids compared with levels of CSG in cells, tissues or bodily fluids of preferably the same type from a normal human control, wherein a change in levels of CSG in the patient versus the normal human control is associated with the presence of a selected cancer.

Without limiting the instant invention, typically, for a quantitative diagnostic assay a positive result indicating the patient being tested has cancer is one in which cells, tissues or bodily fluid levels of the cancer marker, such as CSG, are at least two times higher, and most preferably are at least five times higher, than in preferably the same cells, tissues or bodily fluid of a normal human control.

The present invention also provides a method of diagnosing metastases of selected cancers in a patient having a selected cancer which has not yet metastasized for the onset of metastasis. In the method of the present invention, a human cancer patient suspected of having a selected cancer which may have metastasized (but which was not previously known to have metastasized) is identified. This is accomplished by a variety of means known to those of skill in the art. For example, in the case of ovarian cancer, patients are typically diagnosed with ovarian cancer following surgical staging and monitoring of CA125 levels. Traditional detection methods are also available and well known for other selected cancers which can be diagnosed by determination of CSG levels in a patient.

In the present invention, determining the presence of CSG levels in cells, tissues or bodily fluid, is particularly useful for discriminating between a selected cancer which has not metastasized and a selected cancer which has metastasized. Existing techniques have difficulty discriminating between cancers which have metastasized and cancers which have not metastasized and proper treatment selection is often dependent upon such knowledge.

In the present invention, the cancer marker levels measured in such cells, tissues or bodily fluid is CSG, and are compared with levels of CSG in preferably the same cells, tissue or bodily fluid type of a normal human control. That is, if the cancer marker being observed is CSG in serum, this level is preferably compared with the level of CSG in serum of a normal human patient. An increase in the CSG in the patient versus the normal human control is associated with a cancer which has metastasized.

Without limiting the instant invention, typically, for a quantitative diagnostic assay a positive result indicating the cancer in the patient being tested or monitored has metastasized is one in which cells, tissues or bodily fluid levels of the cancer marker, such as CSG, are at least two times higher, and most preferably are at least five times higher, than in preferably the same cells, tissues or bodily fluid of a normal patient.

Normal human control as used herein includes a human patient without cancer and/or non cancerous samples from the patient; in the methods for diagnosing or monitoring for metastasis, normal human control may also include samples from a human patient that is determined by reliable methods to have a selected cancer which has not metastasized.

Staging

The invention also provides a method of staging selected cancers in human patients. The method comprises identifying a human patient having a selected cancer and analyzing a sample of cells, tissues or bodily fluid from such human patient for CSG. Then, the method compares CSG levels in such cells, tissues or bodily fluid with levels of CSG in preferably the same cells, tissues or bodily fluid type of a normal human control sample, wherein an increase in CSG levels in the human patient versus the normal human control is associated with a cancer which is progressing and a decrease in the levels of CSG is associated with a cancer which is regressing or in remission.

Monitoring

Further provided is a method of monitoring selected cancers in humans for the onset of metastasis. The method comprises identifying a human patient having a selected cancer that is not known to have metastasized; periodically analyzing a sample of cells, tissues or bodily fluid from such human patient for CSG; comparing the CSG levels in such cells, tissues or bodily fluid with levels of CSG in preferably the same cells, tissues or bodily fluid type of a normal human control sample, wherein an increase in CSG levels in the human patient versus the normal human control is associated with a cancer which has metastasized.

Further provided by this invention is a method of monitoring the change in stage of selected cancers in humans having such cancers. The method comprises identifying a human patient having a selected cancer; periodically analyzing a sample of cells, tissues or bodily fluid from such human patient for CSG; comparing the CSG levels in such cells, tissues or bodily fluid with levels of CSG in preferably the same cells, tissues or bodily fluid type of a normal human control sample, wherein an increase in CSG levels in the human patient versus the normal human control is associated with a cancer which is progressing in stage and a decrease in the levels of CSG is associated with a cancer which is regressing in stage or in remission.

Monitoring such patient for onset of metastasis is periodic and preferably done on a quarterly basis. However, this may be more or less frequent depending on the cancer, the particular patient, and the stage of the cancer.

Assay Techniques

Assay techniques that can be used to determine levels of gene expression, such as CSG of the present invention, in a sample derived from a patient are well known to those of skill in the art. Such assay methods include radioimmunoassays, reverse transcriptase PCR (RT-PCR) assays, immunohistochemistry assays, in situ hybridization assays, competitive-binding assays, Western Blot analyses, ELISA assays and proteomic approaches. Among these, ELISAs are frequently preferred to diagnose a gene's expressed protein in biological fluids.

An ELISA assay initially comprises preparing an antibody, if not readily available from a commercial source, specific to CSG, preferably a monoclonal antibody. In addition a reporter antibody generally is prepared which binds specifically to CSG. The reporter antibody is attached to a detectable reagent such as radioactive, fluorescent or enzymatic reagent, for example horseradish peroxidase enzyme or alkaline phosphatase.

To carry out the ELISA, antibody specific to CSG is incubated on a solid support, e.g. a polystyrene dish, that binds the antibody. Any free protein binding sites on the dish are then covered by incubating with a non-specific protein such as bovine serum albumin. Next, the sample to be analyzed is incubated in the dish, during which time CSG binds to the specific antibody attached to the polystyrene dish. Unbound sample is washed out with buffer. A reporter antibody specifically directed to CSG and linked to horseradish peroxidase is placed in the dish resulting in binding of the reporter antibody to any monoclonal antibody bound to CSG. Unattached reporter antibody is then washed out. Reagents for peroxidase activity, including a colorimetric substrate are then added to the dish. Immobilized peroxidase, linked to CSG antibodies, produces a colored reaction product. The amount of color developed in a given time period is proportional to the amount of CSG protein present in the sample. Quantitative results typically are obtained by reference to a standard curve.

A competition assay may be employed wherein antibodies specific to CSG attached to a solid support and labeled CSG and a sample derived from the host are passed over the solid support and the amount of label detected attached to the solid support can be correlated to a quantity of CSG in the sample.

Nucleic acid methods may be used to detect CSG mRNA as a marker for selected cancers. Polymerase chain reaction (PCR) and other nucleic acid methods, such as ligase chain reaction (LCR) and nucleic acid sequence based amplification (NASABA), can be used to detect malignant cells for diagnosis and monitoring of the various selected malignancies. For example, reverse-transcriptase PCR (RT-PCR) is a powerful technique which can be used to detect the presence of a specific mRNA population in a complex mixture of thousands of other mRNA species. In RT-PCR, an mRNA species is first reverse transcribed to complementary DNA (cDNA) with use of the enzyme reverse transcriptase; the cDNA is then amplified as in a standard PCR reaction. RT-PCR can thus reveal by amplification the presence of a single species of mRNA. Accordingly, if the mRNA is highly specific for the cell that produces it, RT-PCR can be used to identify the presence of a specific type of cell.

Hybridization to clones or oligonucleotides arrayed on a solid support (i.e. gridding) can be used to both detect the expression of and quantitate the level of expression of that gene. In this approach, a cDNA encoding the CSG gene is fixed to a substrate. The substrate may be of any suitable type including but not limited to glass, nitrocellulose, nylon or plastic. At least a portion of the DNA encoding the CSG gene is attached to the substrate and then incubated with the analyte, which may be RNA or a complementary DNA (cDNA) copy of the RNA, isolated from the tissue of interest. Hybridization between the substrate bound DNA and the analyte can be detected and quantitated by several means including but not limited to radioactive labeling or fluorescence labeling of the analyte or a secondary molecule designed to detect the hybrid. Quantitation of the level of gene expression can be done by comparison of the intensity of the signal from the analyte compared with that determined from known standards. The standards can be obtained by in vitro transcription of the target gene, quantitating the yield, and then using that material to generate a standard curve.

Of the proteomic approaches, 2D electrophoresis is a technique well known to those in the art. Isolation of individual proteins from a sample such as serum is accomplished using sequential separation of proteins by different characteristics usually on polyacrylamide gels. First, proteins are separated by size using an electric current. The current acts uniformly on all proteins, so smaller proteins move farther on the gel than larger proteins. The second dimension applies a current perpendicular to the first and separates proteins not on the basis of size but on the specific electric charge carried by each protein. Since no two proteins with different sequences are identical on the basis of both size and charge, the result of a 2D separation is a square gel in which each protein occupies a unique spot. Analysis of the spots with chemical or antibody probes, or subsequent protein microsequencing can reveal the relative abundance of a given protein and the identity of the proteins in the sample.

The above tests can be carried out on samples derived from a variety of patients' cells, bodily fluids and/or tissue extracts (homogenates or solubilized tissue) such as from tissue biopsy and autopsy material. Bodily fluids useful in the present invention include blood, urine, saliva or any other bodily secretion or derivative thereof. Blood can include whole blood, plasma, serum or any derivative of blood.

In Vivo Antibody Use

Antibodies against CSG can also be used in vivo in patients suspected of suffering from a selected cancer including lung cancer or gynecologic cancers such as ovarian, breast, endometrial or uterine cancer. Specifically, antibodies against a CSG can be injected into a patient suspected of having a selected cancer for diagnostic and/or therapeutic purposes. The use of antibodies for in vivo diagnosis is well known in the art. For example, antibody-chelators labeled with Indium-111 have been described for use in the radioimmunoscintographic imaging of carcinoembryonic antigen expressing tumors (Sumerdon et al. Nucl. Med. Biol. 1990 17:247-254). In particular, these antibody-chelators have been used in detecting tumors in patients suspected of having recurrent colorectal cancer (Griffin et al. J. Clin. Onc. 1991 9:631-640). Antibodies with paramagnetic ions as labels for use in magnetic resonance imaging have also been described (Lauffer, R. B. Magnetic Resonance in Medicine 1991 22:339-342). Antibodies directed against CSGs can be used in a similar manner. Labeled antibodies against a CSG can be injected into patients suspected of having a selected cancer for the purpose of diagnosing or staging of the disease status of the patient. The label used will be selected in accordance with the imaging modality to be used. For example, radioactive labels such as Indium-111, Technetium-99m or Iodine-131 can be used for planar scans or single photon emission computed tomography (SPECT). Positron emitting labels such as Fluorine-19 can be used in positron emission tomography. Paramagnetic ions such as Gadlinium (III) or Manganese (II) can used in magnetic resonance imaging (MRI). Localization of the label permits determination of the spread of the cancer. The amount of label within an organ or tissue also allows determination of the presence or absence of cancer in that organ or tissue.

For patients diagnosed with a selected cancer, injection of an antibody against a CSG can also have a therapeutic benefit. The antibody may exert its therapeutic effect alone. Alternatively, the antibody is conjugated to a cytotoxic agent such as a drug, toxin or radionuclide to enhance its therapeutic effect. Drug monoclonal antibodies have been described in the art for example by Garnett and Baldwin, *Cancer Research* 1986 46:2407-2412. The use of toxins conjugated to monoclonal antibodies for the therapy of various cancers has also been described by Pastan et al. *Cell* 1986 47:641-648. Yttrium-90 labeled monoclonal antibodies have been described for maximization of dose delivered to the tumor while limiting toxicity to normal tissues (Goodwin and Meares Cancer Supplement 1997 80:2675-2680). Other cytotoxic radionuclides including, but not limited to Copper-67, Iodine-131 and Rhenium-186 can also be used for labeling of antibodies against CSGs.

Antibodies which can be used in these in vivo methods include both polyclonal and monoclonal antibodies and antibodies prepared via molecular biology techniques. Antibody fragments and aptamers and single-stranded oligonucleotides such as those derived from an in vitro evolution protocol referred to as SELEX and well known to those skilled in the art can also be used.

The present invention is further described by the following examples. These examples are provided solely to illustrate the invention by reference to specific embodiments. The exemplifications, while illustrating certain aspects of the invention, do not portray the limitations or circumscribe the scope of the disclosed invention.

EXAMPLES

Example 1

Identification of CSGs were carried out by a systematic analysis of data in the LIFESEQ database available from Incyte Pharmaceuticals, Palo Alto, Calif., using the data mining Cancer Leads Automatic Search Package (CLASP) developed by diaDexus LLC, Santa Clara, Calif.

The CLASP performs the following steps: selection of highly expressed organ specific genes based on the abundance level of the corresponding EST in the targeted organ versus all the other organs; analysis of the expression level of each highly expressed organ specific genes in normal, tumor tissue, disease tissue and tissue libraries associated with tumor or disease. Selection of the candidates demonstrating component ESTs were exclusively or more frequently found in tumor libraries. The CLASP allows the identification of highly expressed organ and cancer specific genes. A final manual in depth evaluation is then performed to finalize the CSGs selection.

TABLE 1

CSG Sequences

| SEQ ID NO: | Clone ID | Gene ID |
|---|---|---|
| 1 | 16656542 | 234617 |
| 2 | 1283171 | 332459 |
| 3 | 1649377 | 481154 |
| 4 | 236044H1 | none assigned |
| 5 | none assigned | 255687 |
| 6 | none assigned | 251313 |
| 7 | none assigned | 12029 |
| 8 | none assigned | 251804 |

The following examples are carried out using standard techniques, which are well known and routine to those of skill in the art, except where otherwise described in detail. Routine molecular biology techniques of the following example can be carried out as described in standard laboratory manuals, such as Sambrook et al., MOLECULAR CLONING: A LABORATORY MANUAL, 2nd Ed.; Cold Spring Harbor Laboratory Press, Cold Spring Harbor, N.Y. (1989).

Example 2

Relative Quantitation of Gene Expression

Real-Time quantitative PCR with fluorescent Taqman probes is a quantitation detection system utilizing the 5'-3' nuclease activity of Taq DNA polymerase. The method uses an internal fluorescent oligonucleotide probe (Taqman) labeled with a 5' reporter dye and a downstream, 3' quencher dye. During PCR, the 5'-3' nuclease activity of Taq DNA polymerase releases the reporter, whose fluorescence can then be detected by the laser detector of the Model 7700 Sequence Detection System (PE Applied Biosystems, Foster City, Calif., USA).

Amplification of an endogenous control is used to standardize the amount of sample RNA added to the reaction and normalize for Reverse Transcriptase (RT) efficiency. Either cyclophilin, glyceraldehyde-3-phosphate dehydrogenase (GAPDH) or 18S ribosomal RNA (rRNA) is used as this endogenous control. To calculate relative quantitation between all the samples studied, the target RNA levels for one sample were used as the basis for comparative results (calibrator). Quantitation relative to the "calibrator" can be obtained using the standard curve method or the comparative method (User Bulletin #2: ABI PRISM 7700 Sequence Detection System).

The tissue distribution and the level of the target gene for every example in normal and cancer tissue were evaluated. Total RNA was extracted from normal tissues, cancer tissues, and from cancers and the corresponding matched adjacent tissues. Subsequently, first strand cDNA was prepared with reverse transcriptase and the polymerase chain reaction was done using primers and Taqman probe specific to each target gene. The results are analyzed using the ABI PRISM 7700 Sequence Detector. The absolute numbers are relative levels of expression of the target gene in a particular tissue compared to the calibrator tissue.

Measurement of Ovr110; Clone ID16656542; Gene ID 234617 (SEQ ID NO:1, 10, 11, 12 or 13)

The absolute numbers depicted in Table 2 are relative levels of expression of Ovr110 (SEQ ID NO:1 or a fragment thereof as depicted in SEQ ID NO:10, 11, 12, or 13) in 12 normal different tissues. All the values are compared to normal stomach (calibrator). These RNA samples are commercially available pools, originated by pooling samples of a particular tissue from different individuals.

TABLE 2

Relative Levels of Ovr110 Expression in Pooled Samples

| Tissue | NORMAL |
|---|---|
| colon | 0.00 |
| endometrium | 8.82 |
| kidney | 7.19 |
| liver | 0.36 |
| ovary | 1.19 |
| pancreas | 21.41 |
| prostate | 2.79 |
| small intestine | 0.03 |
| spleen | 0.00 |
| 00000000000000stomach | 1.00 |
| testis | 8.72 |
| uterus | 0.93 |

The relative levels of expression in Table 2 show that Ovr110 is expressed at comparable levels in most of the normal tissues analyzed. Pancreas, with a relative expression level of 21.41, endometrium (8.82), testis (8.72), and kidney (7.19) are the only tissues expressing high levels of Ovr110 mRNA.

The absolute numbers in Table 2 were obtained analyzing pools of samples of a particular tissue from different individuals. They can not be compared to the absolute numbers originated from RNA obtained from tissue samples of a single individual in Table 3.

The absolute numbers depicted in Table 3 are relative levels of expression of Ovr110 in 73 pairs of matching samples. All the values are compared to normal stomach (calibrator). A matching pair is formed by mRNA from the cancer sample for a particular tissue and mRNA from the normal adjacent sample for that same tissue from the same individual. In addition, 15 unmatched cancer samples (from ovary and mammary gland) and 14 unmatched normal samples (from ovary and mammary gland) were also tested.

TABLE 3

Relative Levels of Ovr110 Expression in Individual Samples

| Sample ID | Tissue | Cancer | Matching Normal Adjacent | Normal |
|---|---|---|---|---|
| Ovr103X | Ovary 1 | 86.22 | 0.53 | |
| Ovr104O | Ovary 2 | 168.31 | | |
| Ovr157 | Ovary 3 | 528.22 | | |
| Ovr63A | Ovary 4 | 1.71 | | |
| Ovr773O | Ovary 5 | 464.65 | | |

TABLE 3-continued

Relative Levels of Ovr110 Expression in Individual Samples

| Sample ID | Tissue | Cancer | Matching Normal Adjacent | Normal |
|---|---|---|---|---|
| Ovr1005O | Ovary 6 | 18.32 | | |
| Ovr1028 | Ovary 7 | 7.78 | | |
| Ovr1118 | Ovary 8 | 0.00 | | |
| Ovr130X | Ovary 9 | 149.09 | | |
| Ovr638A | Ovary 10 | 3.14 | | |
| OvrA1B | Ovary 11 | 21.26 | | |
| OvrA1C | Ovary 12 | 1.83 | | |
| OvrC360 | Ovary 13 | 0.52 | | |
| Ovr18GA | Ovary 14 | | | 1.07 |
| Ovr20GA | Ovary 15 | | | 1.88 |
| Ovr25GA | Ovary 16 | | | 2.52 |
| Ovr206I | Ovary 17 | | | 2.51 |
| Ovr32RA | Ovary 18 | | | 3.01 |
| Ovr35GA | Ovary 19 | | | 5.17 |
| Ovr40G | Ovary 20 | | | 0.45 |
| Ovr50GB | Ovary 21 | | | 2.69 |
| OvrC087 | Ovary 22 | | | 0.47 |
| OvrC179 | Ovary 23 | | | 1.46 |
| OvrC004 | Ovary 24 | | | 4.99 |
| OvrC007 | Ovary 25 | | | 13.36 |
| OvrC109 | Ovary 26 | | | 6.61 |
| MamS516 | Mammary Gland 1 | 16.39 | 13.74 | |
| MamS621 | Mammary Gland 2 | 826.70 | 4.60 | |
| MamS854 | Mammary Gland 3 | 34.60 | 18.30 | |
| Mam59X | Mammary Gland 4 | 721.57 | 27.00 | |
| MamS079 | Mammary Gland 5 | 80.73 | 5.10 | |
| MamS967 | Mammary Gland 6 | 6746.90 | 72.80 | |
| MamS127 | Mammary Gland 7 | 7.00 | 20.00 | |
| MamB011X | Mammary Gland 8 | 1042.00 | 29.00 | |
| Mam12B | Mammary Gland 9 | 1342.00 | | |
| Mam82XI | Mammary Gland 10 | 507.00 | | |
| MamS123 | Mammary Gland 11 | 24.85 | 4.24 | |
| MamS699 | Mammary Gland 12 | 84.74 | 5.54 | |
| MamS997 | Mammary Gland 13 | 482.71 | 11.84 | |
| Mam162X | Mammary Gland 14 | 15.73 | 10.59 | |
| MamA06X | Mammary Gland 15 | 1418.35 | 8.20 | |
| Mam603X | Mammary Gland 16 | 294.00 | | |
| Mam699F | Mammary Gland 17 | 567.40 | 86.60 | |
| Mam12X | Mammary Gland 18 | 425.00 | 31.00 | |
| MamA04 | Mammary Gland 19 | | | 2.00 |
| Mam42DN | Mammary Gland 20 | 46.05 | 31.02 | |
| Utr23XU | Uterus 1 | 600.49 | 27.95 | |
| Utr85XU | Uterus 2 | 73.52 | 18.83 | |
| Utr135XO | Uterus 3 | 178.00 | 274.00 | |
| Utr141XO | Uterus 4 | 289.00 | 26.00 | |
| CvxNKS54 | Cervix 1 | 2.47 | 0.61 | |
| CvxKS83 | Cervix 2 | 1.00 | 2.00 | |
| CvxNKS18 | Cervix 3 | 1.00 | 0.00 | |
| CvxNK23 | Cervix 4 | 5.84 | 14.47 | |
| CvxNK24 | Cervix 5 | 20.32 | 33.13 | |
| End68X | Endometrium 1 | 167.73 | 544.96 | |
| End8963 | Endometrium 2 | 340.14 | 20.89 | |
| End8XA | Endometrium 3 | 1.68 | 224.41 | |
| End65RA | Endometrium 4 | 303.00 | 5.00 | |
| End8911 | Endometrium 5 | 1038.00 | 74.00 | |
| End3AX | Endometrium 6 | 6.59 | 1.69 | |
| End4XA | Endometrium 7 | 0.43 | 15.45 | |
| End5XA | Endometrium 8 | 17.81 | 388.02 | |
| End10479 | Endometrium 9 | 1251.60 | 31.10 | |
| End12XA | Endometrium 10 | 312.80 | 33.80 | |
| Kid107XD | Kidney 1 | 2.68 | 29.65 | |
| Kid109XD | Kidney 2 | 81.01 | 228.33 | |
| Kid10XD | Kidney 3 | 0.00 | 15.30 | |
| Kid6XD | Kidney 4 | 18.32 | 9.06 | |
| Kid11XD | Kidney 5 | 1.38 | 20.75 | |
| Kid5XD | Kidney 6 | 30.27 | 0.19 | |
| Liv15XA | Liver 1 | 0.00 | 0.45 | |
| Liv42X | Liver 2 | 0.81 | 0.40 | |
| Liv94XA | Liver 3 | 12.00 | 2.16 | |
| Lng LC71 | Lung 1 | 5.45 | 3.31 | |
| LngAC39 | Lung 2 | 1.11 | 0.00 | |
| LngBR94 | Lung 3 | 4.50 | 0.00 | |
| LngSQ45 | Lung 4 | 15.03 | 0.76 | |
| LngC20X | Lung 5 | 0.00 | 1.65 | |
| LngSQ56 | Lung 6 | 91.77 | 8.03 | |
| ClnAS89 | Colon 1 | 0.79 | 7.65 | |
| ClnC9XR | Colon 2 | 0.03 | 0.00 | |
| ClnRC67 | Colon 3 | 0.00 | 0.00 | |
| ClnSG36 | Colon 4 | 0.81 | 0.35 | |
| ClnTX89 | Colon 5 | 0.00 | 0.00 | |
| ClnSG45 | Colon 6 | 0.00 | 0.06 | |
| ClnTX01 | Colon 7 | 0.00 | 0.00 | |
| Pan77X | Pancreas 1 | 0.89 | 2.62 | |
| Pan71XL | Pancreas 2 | 3.99 | 0.12 | |
| Pan82XP | Pancreas 3 | 59.92 | 28.44 | |
| Pan92X | Pancreas 4 | 17.21 | 0.00 | |
| StoAC93 | Stomach 1 | 7.54 | 6.43 | |
| StoAC99 | Stomach 2 | 19.49 | 3.19 | |
| StoAC44 | Stomach 3 | 3.62 | 0.37 | |
| SmI21XA | Small Intestine 1 | 0.00 | 0.00 | |
| SmIH89 | Small Intestine 2 | 0.00 | 0.00 | |
| Bld32XK | Bladder 1 | 0.00 | 0.21 | |
| Bld46XK | Bladder 2 | 0.36 | 0.32 | |
| BldTR17 | Bladder 3 | 0.28 | 0.00 | |
| Tst39X | Testis | 11.24 | 2.24 | |
| Pro84XB | Prostate 1 | 2.60 | 24.30 | |
| Pro90XB | Prostate 2 | 1.40 | 2.00 | |

0.00 = Negative

Table 2 and Table 3 represent a combined total of 187 samples in 16 different tissue types. In the analysis of matching samples, the higher levels of expression were in mammary gland, uterus, endometrium and ovary, showing a high degree of tissue specificity for the gynecologic tissues. Of all the samples different than those mentioned before analyzed, only a few samples (Kid109XD, LngSQ56, and Pan82XP) showed high levels of expression of Ovr110.

Furthermore, the level of mRNA expression was compared in cancer samples and the isogenic normal adjacent tissue from the same individual. This comparison provides an indication of specificity for the cancer stage (e.g. higher levels of mRNA expression in the cancer sample compared to the normal adjacent). Table 3 shows overexpression of Ovr110 in 15 of 16 mammary gland cancer tissues compared with their respective normal adjacent (mammary gland samples MamS516, MamS621, MamS854, Mam59X, MamS079, MamS967, MamB011X, MamS123, MamS699, MamS997, Mam162X, MamA06X, Mam699F, Mam12X, and Mam42DN). There was overexpression in the cancer tissue for 94% of the mammary gland matching samples tested.

For uterus, Ovr110 is overexpressed in 3 of 4 matching samples (uterus samples Utr23XU, Utr85XU, and Utr141XO). There was overexpression in the cancer tissue for 75% of the uterus matching samples analyzed.

For endometrium, Ovr110 is overexpressed in 6 of 10 matching samples (endometrium samples End8963, End65RA, End8911, End3AX, End10479, and End12XA). There was overexpression in the cancer tissue for 60% of the endometrium matching samples.

For ovary, Ovr110 shows overexpression in 1 of 1 matching sample. For the unmatched ovarian samples, 8 of 12 cancer samples show expression values of Ovr110 higher than the median (2.52) for the normal unmatched ovarian samples. There was overexpression in the cancer tissue for 67% of the unmatched ovarian samples.

Altogether, the level of tissue specificity, plus the mRNA overexpression in most of the matching samples tested are indicative of Ovr110 (including SEQ ID NO:1, 10, 11, 12 or 13) being a diagnostic marker for gynecologic cancers, specifically, mammary gland or breast, uterine, ovarian and endometrial cancer.

Measurement of Ovr114; Clone ID1649377; Gene ID 481154 (SEQ ID NO:3)

The numbers depicted in Table 4 are relative levels of expression in 12 normal tissues of Ovr114 compared to pancreas (calibrator). These RNA samples were obtained commercially and were generated by pooling samples from a particular tissue from different individuals.

TABLE 4

Relative Levels of Ovr114 Expression in Pooled Samples

| Tissue | Normal |
|---|---|
| Colon | 2.3 |
| Endometrium | 7.6 |
| Kidney | 0.5 |
| Liver | 0.6 |
| Ovary | 5.2 |
| Pancreas | 1.0 |
| Prostate | 2.1 |
| Small Intestine | 1.3 |
| Spleen | 2.4 |
| Stomach | 1.5 |
| Testis | 15.8 |
| Uterus | 8.8 |

The relative levels of expression in Table 4 show that Ovr114 mRNA expression is detected in all the pools of normal tissues analyzed.

The tissues shown in Table 4 are pooled samples from different individuals. The tissues shown in Table 5 were obtained from individuals and are not pooled. Hence the values for mRNA expression levels shown in Table 4 cannot be directly compared to the values shown in Table 5.

The numbers depicted in Table 5 are relative levels of expression of Ovr114 compared to pancreas (calibrator), in 46 pairs of matching samples and 27 unmatched tissue samples. Each matching pair contains the cancer sample for a particular tissue and the normal adjacent tissue sample for that same tissue from the same individual. In cancers (for example, ovary) where it was not possible to obtain normal adjacent samples from the same individual, samples from a different normal individual were analyzed.

TABLE 5

Relative Levels of Ovr114 Expression in Individual Samples

| Tissue | Sample ID | Cancer Type | Cancer | Borderline Malignant | Normal & Matching Normal Adjacent |
|---|---|---|---|---|---|
| Ovary 1 | Ovr1037O/1038O | Papillary serous adenocarcinoma, G3 | 17.04 | | 3.93 |
| Ovary 2 | OvrG021SPI/SN2 | Papillary serous adenocarcinoma | 1.62 | | 4.34 |
| Ovary 3 | OvrG010SP/SN | Papillary serous adenocarcinoma | 0.50 | | 1.12 |
| Ovary 4 | OvrA081F/A082D | Mucinous tumor, low malignant potential | | 0.84 | 0.96 |
| Ovary 5 | OvrA084/A086 | Mucinous tumor, grade G-B, borderline | | 5.24 | 6.00 |
| Ovary 6 | Ovr14604A1C | Serous cystadenofibroma, low malignancy | | 5.33 | |
| Ovary 7 | Ovr14638A1C | Follicular cysts, low malignant potential | | 8.11 | |
| Ovary 8 | Ovr1040O | Papillary serous adenocarcinoma, G2 | 13.27 | | |
| Ovary 9 | Ovr1157O | Papillary serous adenocarcinoma | 106.08 | | |
| Ovary 10 | Ovr1005O | Papillary serous endometricarcinoma | 77.04 | | |
| Ovary 11 | Ovr1028O | Ovarian carcinoma | 14.78 | | |
| Ovary 12 | Ovr14603A1D | Adenocarcinoma | 22.23 | | |
| Ovary 13 | Ovr9410C360 | Endometrioid adenocarcinoma | 4.74 | | |
| Ovary 14 | Ovr1305X | Papillary serous adenocarcinoma | 96.49 | | |
| Ovary 15 | Ovr773O | Papillary serous adenocarcinoma | 8.40 | | |
| Ovary 16 | Ovr988Z | Papillary serous adenocarcinoma | 6.40 | | |
| Ovary 17 | Ovr9702C018GA | Normal Cystic | | | 12.06 |

TABLE 5-continued

Relative Levels of Ovr114 Expression in Individual Samples

| Tissue | Sample ID | Cancer Type | Cancer | Borderline Malignant | Normal & Matching Normal Adjacent |
|---|---|---|---|---|---|
| Ovary 18 | Ovr2061 | Normal left atrophic, small cystic | | | 10.11 |
| Ovary 19 | Ovr9702C020GA | Normal-multiple ovarian cysts | | | 12.70 |
| Ovary 20 | Ovr9702C025GA | Normal-hemorrhage CL cysts | | | 22.09 |
| Ovary 21 | Ovr9701C050GB | Normal-multiple ovarian cysts | | | 9.01 |
| Ovary 22 | Ovr9701C087RA | Normal-small follicle cysts | | | 1.86 |
| Ovary 23 | Ovr9702C032RA | | | | 7.81 |
| Ovary 24 | Ovr9701C109RA | Normal | | | 1.50 |
| Ovary 25 | Ovr9411C057R | Benign large endometriotic cyst | | | 5.22 |
| Ovary 26 | Ovr9701C179a | Normal | | | 3.09 |
| Ovary 27 | Ovr1461O | Serous cystadenofibroma, no malignancy | | | 3.53 |
| Ovary 28 | Ovr9701C035GA | Normal | | | 6.32 |
| Ovary 29 | Ovr9702C007RA | Normal | | | 0 |
| Ovary 30 | Ovr9701C087RA | Normal-small follicle cysts | | | 1.97 |
| Ovary 31 | Ovr9411C109 | Normal | | | 9.49 |
| Ovary 32 | Ovr9701C177a | Normal-cystic follicles | | | 3.85 |
| Endometrium 1 | End14863A1A/A2A | Moderately differ. Endome. carcinoma/NAT | 1.30 | | 0.70 |
| Endometrium 2 | End9709C056A/55A | Endometrial adenocarcinoma/NAT | 1.83 | | 11.90 |
| Endometrium 3 | End9704C281A/2A | Endometrial adenocarcinoma/NAT | 13.32 | | 7.76 |
| Endometrium 4 | End9705A125A/6A | Endometrial adenocarcinoma/NAT | 3.62 | | 3.34 |
| Mammary Gland 1 | Mam00042D01/N01 | | 3.13 | | 0.76 |
| Mammary Gland 2 | MamS99-522A/B | | 4.45 | | 0.45 |
| Mammary Gland 3 | Mam1620F/1621F | | 0.74 | | 1.91 |
| Mammary Gland 4 | Mam4003259a/g | | 3.48 | | 2.00 |
| Uterus 1 | Utr850U/851U | Stage 1 endometrial cancer/NAT | 46.96 | | 11.96 |
| Uterus 2 | Utr233U96/234U96 | Adenocarcinoma/NAT | 20.02 | | 5.90 |
| Uterus 3 | Utr1359O/1358O | Tumor/NAT | 10.23 | | 7.74 |
| Uterus 4 | Utr1417O/1418O | Malignant tumor/NAT | 7.52 | | 4.92 |
| Cervix 1 | CvxVNM00083/83 | Keratinizing squamous cell carcinoma | 5.47 | | 14.31 |
| Cervix 2 | CvxIND00023D/N | Large cell nonkeratinizing carcinoma | 4.99 | | 3.99 |
| Cervix 3 | CvxIND00024D/N | Large cell nonkeratinizing carcinoma | 10.14 | | 14.22 |
| Bladder 1 | Bld665T/664T | | 1.43 | | 4.03 |
| Bladder 2 | Bld327K/328K | Papillary transitional cell carcinoma/NAT | 1.15 | | 0.99 |
| Kidney 1 | Kid4003710C/F | | 0.03 | | 0.35 |
| Kidney 2 | Kid1242D/1243D | | 1.61 | | 0.14 |
| Lung 1 | Lng750C/751C | Metastatic osteogenic sarcoma/NAT | 2.44 | | 5.73 |
| Lung 2 | Lng8890A/8890B | Cancer/NAT | 1.11 | | 5.19 |
| Lung 3 | Lng9502C109R/10R | | 1.99 | | 0.80 |
| Liver 1 | Liv1747/1743 | Hepatocellular carcinoma/NAT | 0.67 | | 1.07 |
| Liver 2 | LivVNM00175/175 | Cancer/NAT | 15.46 | | 2.85 |
| Skin 1 | Skn2S9821248A/B | Secondary malignant melanoma | 2.83 | | 0.70 |
| Skin 2 | Skn4005287A1/B2 | | 0.91 | | 4.02 |
| Small Int. 1 | SmI9802H008/009 | | 0.87 | | 0.82 |
| Stomach 1 | Sto4004864A4/B4 | Adenocarcinoma/NAT | 0.81 | | 1.22 |
| Stomach 2 | StoS9822539A/B | Adenocarcinoma/NAT | 1.22 | | 1.39 |
| Stomach 3 | StoS99728A/C | Malignant gastrointestinal stromal tumor | 0.47 | | 0.35 |
| Prostate 1 | Pro1012B/1013B | Adenocarcinoma/NAT | 2.39 | | 2.61 |
| Prostate 2 | Pro1094B/1095B | | 0.10 | | 0.38 |

TABLE 5-continued

Relative Levels of Ovr114 Expression in Individual Samples

| Tissue | Sample ID | Cancer Type | Cancer | Borderline Malignant | Normal & Matching Normal Adjacent |
|---|---|---|---|---|---|
| Pancreas 1 | Pan776p/777p | Tumor/NAT | 2.39 | | 0.52 |
| Pancreas 2 | Pan824p/825p | Cystic adenoma | 1.66 | | 1.22 |
| Testis 1 | Tst239X/240X | Tumor/NAT | 1.24 | | 1.72 |
| Colon 1 | Cln9706c068ra/69ra | Adenocarcinoma/NAT | 0.38 | | 0.65 |
| Colon 2 | Cln4004732A7/B6 | Adenocarcinoma/NAT | 0.44 | | 1.26 |
| Colon 3 | Cln4004695A9/B8 | | 1.94 | | 1.53 |
| Colon 4 | Cln9612B006/005 | Asc. Colon, Cecum, adenocarcinoma | 3.38 | | 1.10 |
| Colon 5 | Cln9704C024R/25R | Adenocarcinoma/NAT | 1.66 | | 2.77 |

Table 4 and Table 5 represent a combined total of 129 samples in 17 human tissue types. Among 117 samples in Table 5 representing 16 different tissues high levels of expression are seen only in ovarian cancer samples. The median expression of Ovr114 is 14.03 (range: 0.5-106.08) in ovarian cancer and 4.34 (range: 0-22.09) in normal ovaries. In other words, the median expression levels of Ovr114 in cancer samples is increased 3.5 fold as compared with that of the normal ovarian samples. Five of 12 ovarian cancers (42%) showed increased expression relative to normal ovary (with 95% specificity). The median expression of Ovr114 in other gynecologic cancers is 4.99, and 2 out of 15 samples showed expression levels comparable with that in ovarian cancer. The median of the expression levels of Ovr114 in the rest of the cancer samples is 1.24, which is more than 11 fold less than that detected in ovarian cancer samples. No individual showed an expression level comparable to that of ovarian cancer samples (except Liver 2; LivVNM00175/175).

The 3.5 fold increase in expression in 42% of the individual ovarian cancer samples and no compatible expression in other non-gynecologic cancers is indicative of Ovr114 being a diagnostic marker for detection of ovarian cancer cells. It is believed that the Ovr114 marker may also be useful in detection of additional gynecologic cancers.

Measurement of Ovr115; Clone ID1283171; Gene ID 332459 (SEQ ID NO:2 or 14)

The numbers depicted in Table 6 are relative levels of expression Ovr115 compared to their respective calibrators. The numbers are relative levels of expression in 12 normal tissues of ovaries compared to Testis (calibrator). These RNA samples were obtained commercially and were generated by pooling samples from a particular tissue from different individuals.

TABLE 6

Relative Levels of Ovr115 Expression in Pooled Samples

| Tissue | Normal |
|---|---|
| Colon | 858.10 |
| Endometrium | 12.34 |
| Kidney | 3.76 |
| Liver | 0.00 |
| Ovary | 0.43 |
| Pancreas | 0.00 |
| Prostate | 8.91 |
| Small Intestine | 62.25 |
| Spleen | 0.00 |
| Stomach | 37.53 |
| Testis | 1.00 |
| Uterus | 47.67 |

The relative levels of expression in Table 6 show that Ovr115 mRNA expression is detected in all the 12 normal tissue pools analyzed.

The tissues shown in Table 6 are pooled samples from different individuals. The tissues shown in Table 7 were obtained from individuals and are not pooled. Hence the values for mRNA expression levels shown in Table 6 cannot be directly compared to the values shown in Table 7.

The numbers depicted in Table 7 are relative levels of expression of Ovr115 compared to testis (calibrator), in 46 pairs of matching samples and 27 unmatched tissue samples. Each matching pair contains the cancer sample for a particular tissue and the normal adjacent tissue sample for that same tissue from the same individual. In cancers (for example, ovary) where it was not possible to obtain normal adjacent samples from the same individual, samples from a different normal individual were analyzed.

TABLE 7

Relative Levels of Ovr115 Expression in Individual Samples

| Tissue | Sample ID | Cancer Type | Cancer | Borderline Malignant | Normal & Matching Normal Adjacent |
|---|---|---|---|---|---|
| Ovary 1 | Ovr1037O/1038O | Papillary serous adenocarcinoma, G3 | 193.34 | | 0.24 |
| Ovary 3 | OvrG021SPI/SN2 | Papillary serous adenocarcinoma | 0.38 | | 0.31 |
| Ovary 4 | OvrG010SP/SN | Papillary serous adenocarcinoma | 231.25 | | 0.45 |
| Ovary 2 | OvrA084/A086 | Mucinous tumor, grade G-B, borderline | | 143.34 | 16.65 |

TABLE 7-continued

Relative Levels of Ovr115 Expression in Individual Samples

| Tissue | Sample ID | Cancer Type | Cancer | Borderline Malignant | Normal & Matching Normal Adjacent |
|---|---|---|---|---|---|
| Ovary 5 | OvrA081F/A082D | Mucinous tumor, low malignant potential | | 314.13 | 0 |
| Ovary 19 | Ovr14604A1C | Serous cystadenofibroma, low malignancy | | 299.87 | |
| Ovary 26 | Ovr14638A1C | Follicular cysts, low malignant potential | | 1278.32 | |
| Ovary 6 | Ovr1040O | Papillary serous adenocarcinoma, G2 | 144.25 | | |
| Ovary 22 | Ovr9410C360 | Endometrioid adenocarcinoma | 0.29 | | |
| Ovary 23 | Ovr1305X | Papillary serous adenocarcinoma | 157.41 | | |
| Ovary 27 | Ovr773O | Papillary serous adenocarcinoma | 340.04 | | |
| Ovary 28 | Ovr988Z | Papillary serous adenocarcinoma | 464.75 | | |
| Ovary 7 | Ovr1157O | Papillary serous adenocarcinoma | 432.07 | | |
| Ovary 8 | Ovr11005O | Papillary serous endometricarcinoma | 74.23 | | |
| Ovary 9 | Ovr1028O | Ovarian carcinoma | 1408.79 | | |
| Ovary 10 | Ovr14603A1D | Adenocarcinoma | 0.00 | | |
| Ovary 11 | Ovr9702C018GA | Normal Cystic | | | 0.16 |
| Ovary 12 | Ovr2061 | Normal left atrophic, small cystic | | | 0.00 |
| Ovary 13 | Ovr9702C020GA | Normal-multiple ovarian cysts | | | 0.00 |
| Ovary 14 | Ovr9702C025GA | Normal-hemorrhage CL cysts | | | 0.00 |
| Ovary 15 | Ovr9701C050GB | Normal-multiple ovarian cysts | | | 0.91 |
| Ovary 16 | Ovr9701C087RA | Normal-small follicle cysts | | | 0.00 |
| Ovary 17 | Ovr9702C032RA | | | | 0.28 |
| Ovary 18 | Ovr9701C109RA | Normal | | | 0.00 |
| Ovary 20 | Ovr9411C057R | Benign large endometriotic cyst | | | 38.87 |
| Ovary 21 | Ovr9701C179a | Normal | | | 0.08 |
| Ovary 24 | Ovr1461O | Serous cystadenofibroma, no malignancy | | | 0.00 |
| Ovary 25 | Ovr9701C035GA | Normal | | | 0.00 |
| Ovary 29 | Ovr9702C007RA | Normal | | | 0.00 |
| Ovary 30 | Ovr9701C087RA | Normal-small follicle cysts | | | 0.00 |
| Ovary 31 | Ovr9411C109 | Normal | | | 0.00 |
| Ovary 32 | Ovr9701C177a | Normal-cystic follicles | | | 0.00 |
| Uterus 1 | Utr850U/851U | Stage 1 endometrial cancer/NAT | 39.95 | | 13.60 |
| Uterus 2 | Utr233U96/234U96 | Adenocarcinoma/NAT | 140.37 | | 22.67 |
| Uterus 3 | Utr1359O/1358) | Tumor/NAT | 16.45 | | 32.50 |
| Uterus 4 | Utr1417O/1418O | Malignant tumor/NAT | 288.52 | | 5.29 |
| Endometrium 1 | End14863A1A/A2A | Moderately differ. Endome. carcinoma/NAT | 2.61 | | 6.24 |
| Endometrium 2 | End9709C056A/55A | Endometrial adenocarcinoma/NAT | 2.10 | | 49.40 |
| Endometrium 3 | End9704C281A/2A | Endometrial adenocarcinoma/NAT | 480.77 | | 19.22 |
| Endometrium 4 | End9705A125A/6A | Endometrial adenocarcinoma/NAT | 322.07 | | 31.08 |
| Lung 1 | Lng750C/751C | Metastatic osteogenic sarcoma/NAT | 38.81 | | 7.36 |
| Lung 2 | Lng8890A/8890B | Cancer/NAT | 690.12 | | 14.71 |
| Lung 3 | Lng9502C109R/10R | | 1756.90 | | 2.86 |
| Skin 1 | Skn2S9821248A/B | Secondary malignant melanoma | 10.56 | | 0.00 |
| Skin 2 | Skn4005287A1/B2 | | 331.30 | | 47.23 |
| Prostate 1 | Pro1012B/1013B | Adenocarcinoma/NAT | 14.64 | | 4.39 |
| Prostate 2 | Pro1094B/1095B | | 0.09 | | 2.54 |
| Bladder 1 | Bld665T/664T | | 404.56 | | 90.20 |
| Bladder 2 | Bld327K/328K | Papillary transitional cell carcinoma/NAT | 77.35 | | 177.37 |
| Kidney 1 | Kid4003710C/F | | 0.17 | | 12.72 |

TABLE 7-continued

Relative Levels of Ovr115 Expression in Individual Samples

| Tissue | Sample ID | Cancer Type | Cancer | Borderline Malignant | Normal & Matching Normal Adjacent |
|---|---|---|---|---|---|
| Kidney 2 | Kid1242D/1243D | | 0.00 | | 13.74 |
| Mammary Gland 1 | Mam1620F/1621F | | 0.27 | | 0.12 |
| Mammary Gland 2 | Mam4003259a/g | | 5.71 | | 0.00 |
| Liver 1 | Liv1747/1743 | Hepatocellular carcinoma/NAT | 0.14 | | 0.69 |
| Liver 2 | LivVNM00175/175 | Cancer/NAT | 0.00 | | 0.00 |
| Small Int. 1 | SmI9802H008/009 | | 128.44 | | 151.38 |
| Stomach 1 | Sto4004864A4/B4 | Adenocarcinoma/NAT | 303.01 | | 116.72 |
| Stomach 2 | StoS9822539A/B | Adenocarcinoma/NAT | 24.12 | | 17.76 |
| Stomach 3 | StoS99728A/C | Malignant gastrointestinal stromal tumor | 0.00 | | 9.10 |
| Pancreas 1 | Pan776p/777p | Tumor/NAT | 0.00 | | 0.43 |
| Pancreas 2 | Pan824p/825p | Cystic adenoma | 0.00 | | 3.17 |
| Testis 1 | Tst239X/240X | Tumor/NAT | 24.05 | | 1.37 |
| Colon 1 | Cln9706c068ra/69ra | Adenocarcinoma/NAT | 605.60 | | 169.77 |
| Colon 2 | Cln4004732A7/B6 | Adenocarcinoma/NAT | 367.20 | | 281.32 |
| Colon 3 | Cln4004695A9/B8 | | 316.15 | | 295.77 |
| Colon 4 | Cln9612B006/005 | Asc. Colon. Cecum, adenocarcinoma | 820.89 | | 543.52 |
| Colon 5 | Cln9704C024R/25R | Adenocarcinoma/NAT | 161.18 | | 150.07 |
| Cervix 1 | CvxVNM00083/83 | Keratinizing squamous cell carcinoma | 738.17 | | 1195.88 |
| Cervix 2 | CvxIND00023D/N | Large cell nonkeratinizing carcinoma | 1473.04 | | 1229.80 |
| Cervix 3 | CvxIND00024D/N | Large cell nonkeratinizing carcinoma | 2877.48 | | 1275.02 |

Table 6 and Table 7 represent a combined total of 129 samples in 17 human tissue types. Comparisons of the level of mRNA expression in ovarian cancer samples and the normal adjacent tissue from the same individuals or normal tissues from other individuals are shown in Table 7. Ovr115 was expressed at higher levels in 9 of 12 cancer tissues (75%), relative to the maximum level detected in all 21 normal or normal adjacent ovarian samples. All 4 of 4 (100%) ovarian tumors with borderline malignancy had elevated Ovr115 expression. The median expression in ovarian cancers (including the ones with borderline malignancy) was 212.30 while the median expression in normal ovaries was 0. When compared with their own normal adjacent tissue samples, expression levels of Ovr115 were also elevated in 3 of 3 (100%) lung cancers, 3 of 4 (75%) uterus cancers and 2 of 4 (50%) endometrial cancers.

The relatively high expression levels of Ovr115 in ovarian and other selected cancer samples is indicative of Ovr115 being a diagnostic marker for detection of ovarian, lung, uterine and endometrial cancer.

A homolog of Ovr115 has also been identified in public data base; g2597613 as gi|2507612|gb|U75329.1|HSU75329 Human serine protease mRNA, complete CDS. This homolog is depicted herein as SEQ ID NO:9. It is believed that SEQ ID NO:9 or the protein encoded thereby (SEQ ID NO:15) may also be useful as a diagnostic marker for detection of ovarian, lung, uterine and endometrial cancer in human patients.

What is claimed is:

1. A method of treating ovarian, uterine, endometrial or breast cancer in a patient comprising administering to the patient an antibody which binds to a protein encoded by polynucleotide sequence SEQ ID NO:1 or a fragment thereof, wherein the fragment of the protein encoded by polynucleotide sequence SEQ ID NO:1 is encoded by polynucleotide sequence SEQ ID NO:12 or SEQ ID NO:13.

2. The method of claim 1 wherein the antibody is conjugated to a cytotoxic agent.

* * * * *